United States Patent [19]

Matsutani et al.

[11] Patent Number: 5,001,323
[45] Date of Patent: Mar. 19, 1991

[54] METHOD AND APPARATUS FOR MANUFACTURING SURGICAL NEEDLE

[75] Inventors: Kanji Matsutani; Masamitsu Matsutani; Tadashi Otsuka; Yoshimasa Tochimura, all of Tochigi, Japan

[73] Assignee: Matsutani Seisakusho Co., Ltd., Tochigi, Japan

[21] Appl. No.: 447,614

[22] Filed: Dec. 8, 1989

Related U.S. Application Data

[62] Division of Ser. No. 208,053, Jun. 17, 1988, Pat. No. 4,935,029.

[30] Foreign Application Priority Data

Jun. 22, 1987 [JP] Japan .................. 62-153558
Jun. 22, 1987 [JP] Japan .................. 62-153560

[51] Int. Cl.$^5$ .............................. B23K 56/00
[52] U.S. Cl. ................... 219/121.63; 219/121.64; 219/121.82; 219/121.77; 219/121.84
[58] Field of Search ........... 219/121.6, 121.63, 121.64, 219/121.76, 121.82, 121.84, 121.77

[56] References Cited

U.S. PATENT DOCUMENTS 3,835,912  9/1974  Kristensen et al. ........ 219/121.64 X
4,291,218  9/1981  Myhre ....................... 219/121.82 X
4,358,658  11/1982 Van Blarigan et al. .... 219/121.82 X
4,733,047  3/1988  Cruickshank et al. ......... 219/121.63
4,794,231  12/1988 Banas et al. ................ 219/121.64 X Primary Examiner—C. L. Albritton
Attorney, Agent, or Firm—Fish & Richardson

[57] ABSTRACT

In a surgical needle, marks of welding are left as they are on a welded portion between needle and pipe members so that the welded portion has a surface distinguishable from peripheral surfaces of the respective needle and pipe members. The welded portion may be composed of a plurality of peripherally spaced welded parts. In a manufacturing method of the surgical needle, a beam energy is applied from a beam energy emitting arrangement, toward an abutting line between the needle and pipe members, from a direction substantially perpendicular to the needle and pipe members, thereby welding them to each other. In a manufacturing apparatus, a rotational support arrangement is provided for supporting the needle and pipe members in such a manner that end faces of the respective needle and pipe members are abutted against each other at a location coincident with an optical axis of the laser beam, and for rotating the needle and pipe members about their respective axes.

16 Claims, 10 Drawing Sheets

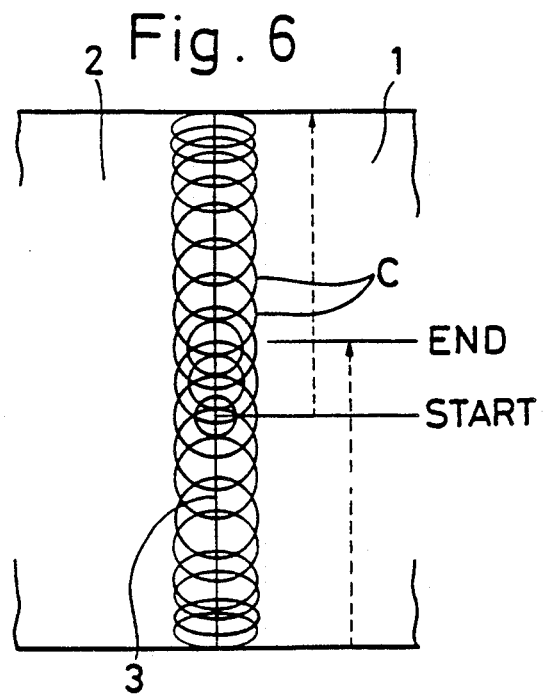
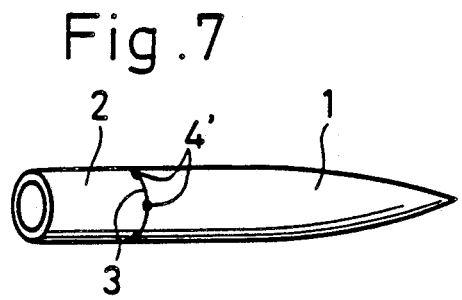
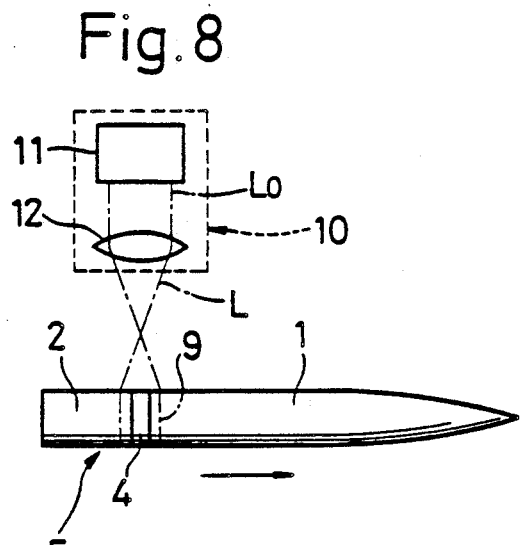
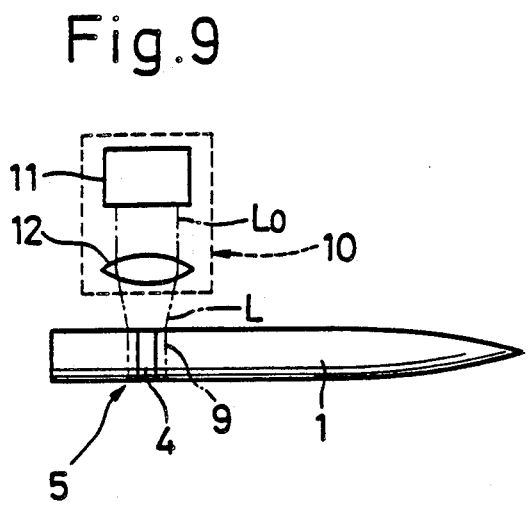
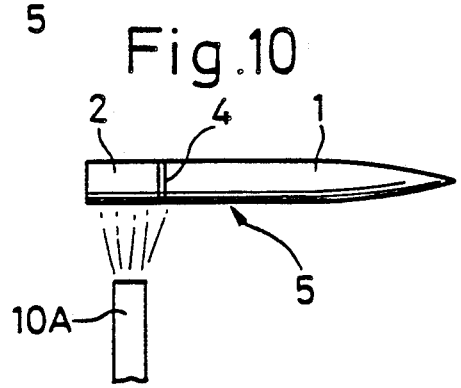
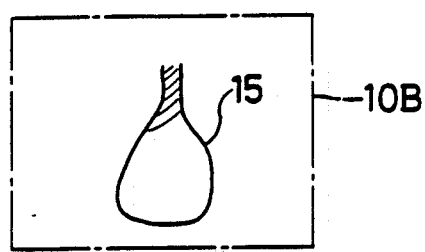

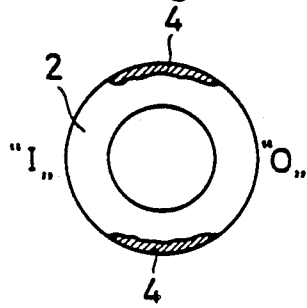
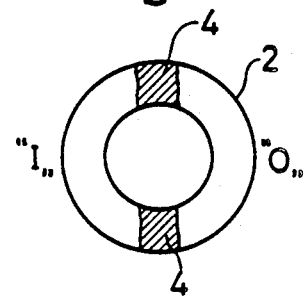
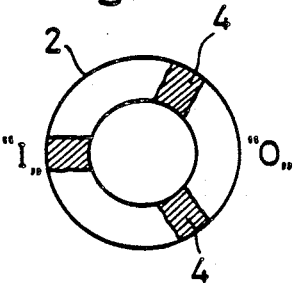
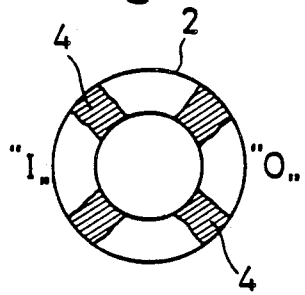
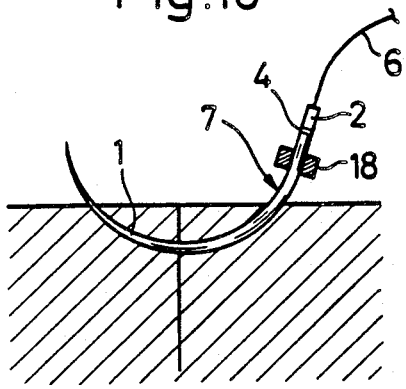
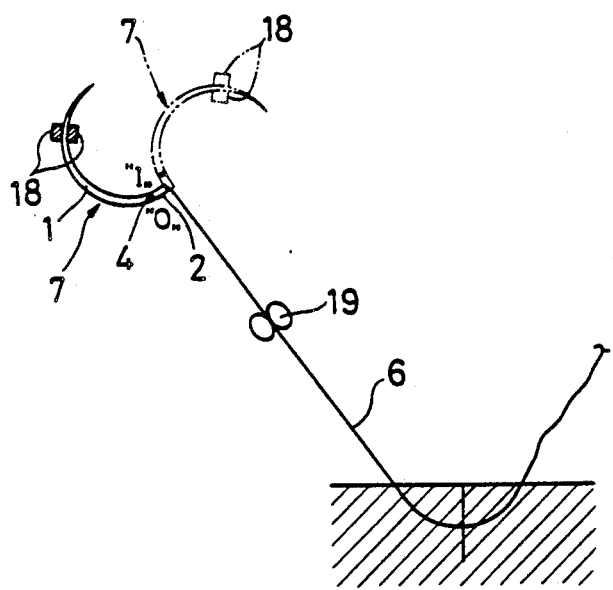
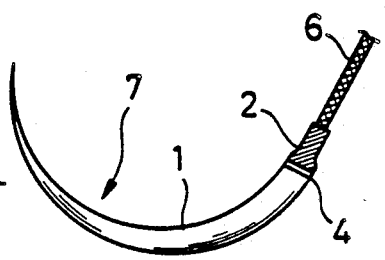

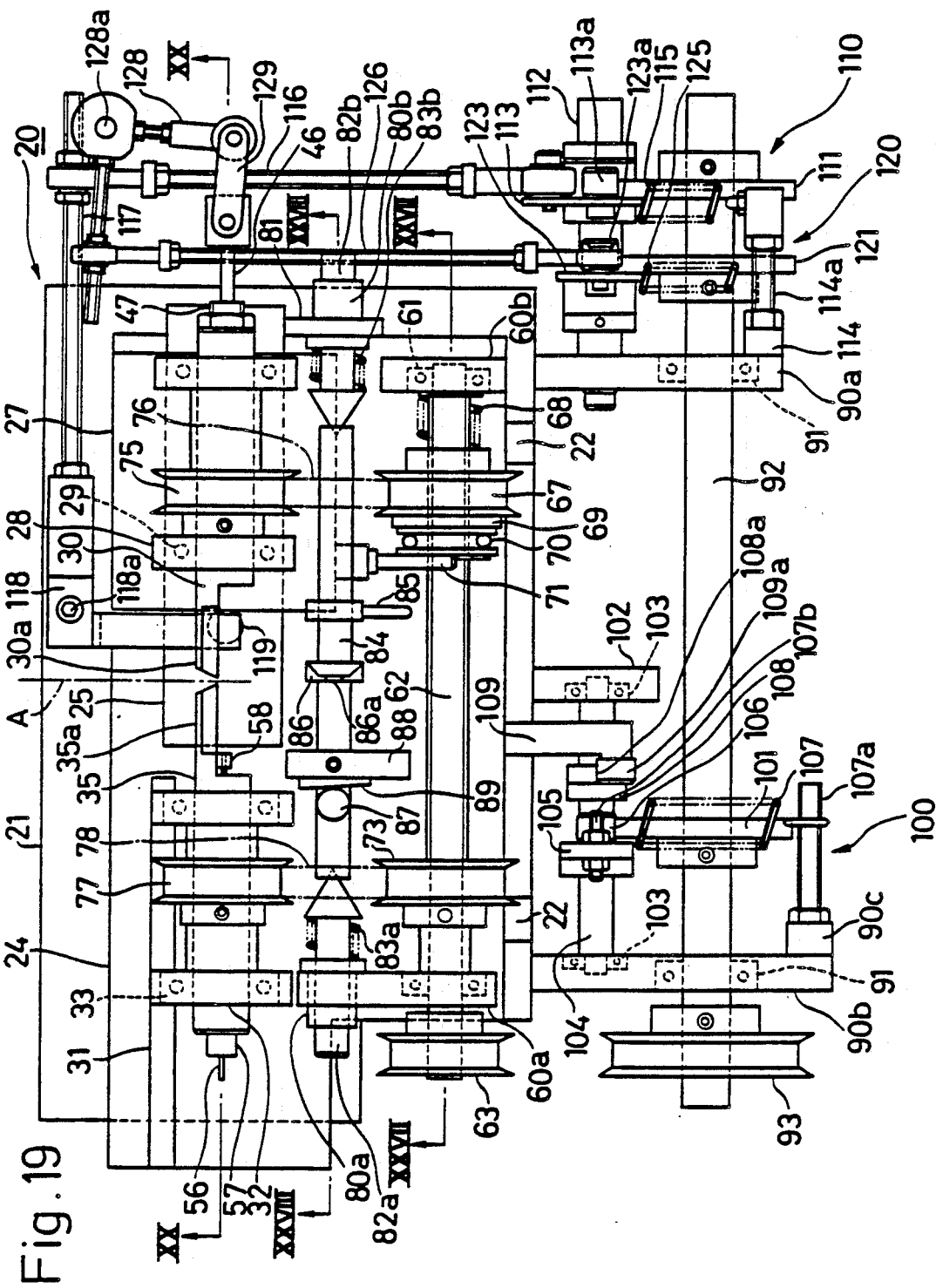

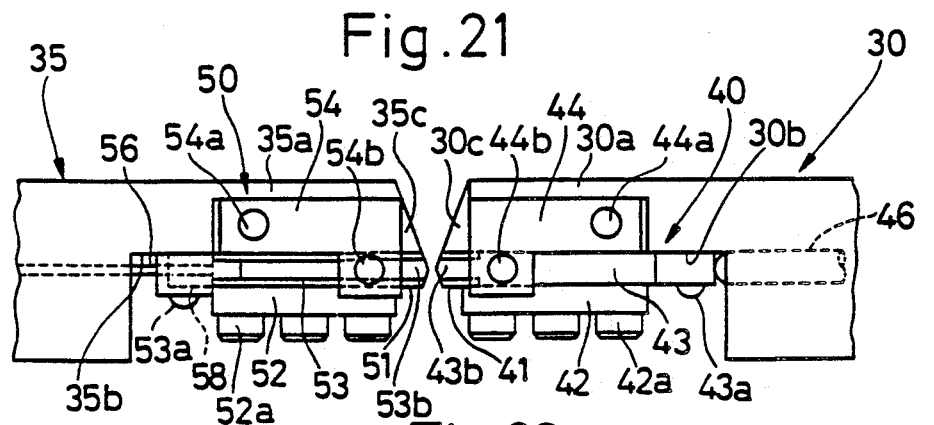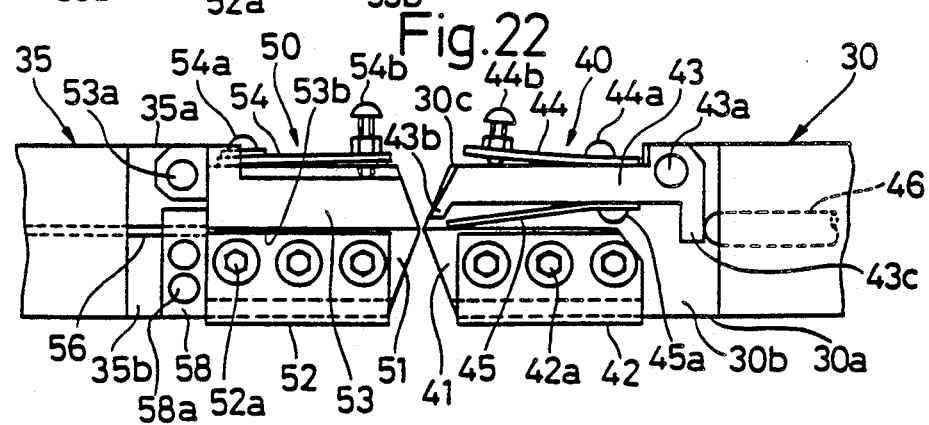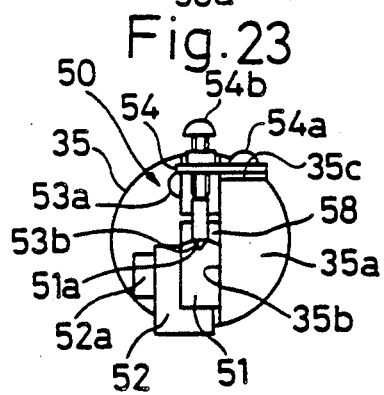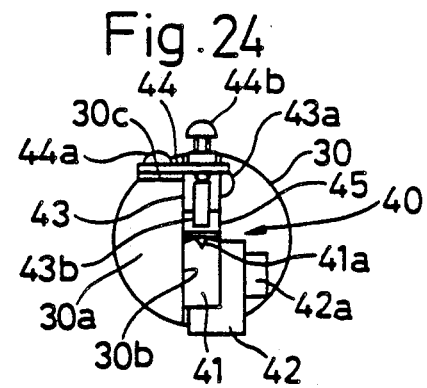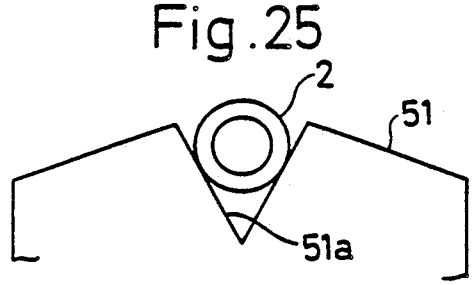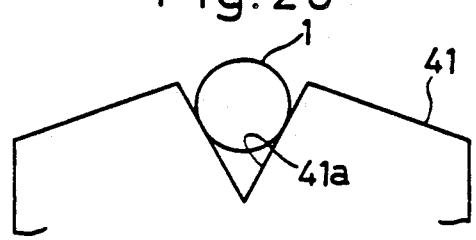

METHOD AND APPARATUS FOR MANUFACTURING SURGICAL NEEDLE

This application is a division of Ser. No. 07/208,053, filed June 17, 1988, now U.S. Pat. No. 4,935,029.

BACKGROUND OF THE INVENTION

The present invention relates to a surgical needle of eyeless type, a method of manufacturing the needle, and an apparatus for carrying out the method.

A surgical needle of eyeless type is known, in which a bore is formed in a proximal end of the needle and extends along an axis thereof. An end of a suture is inserted into the bore in the proximal end of the needle, and the proximal end of the needle is then staked, whereby the suture can be attached to the needle. Usually, there are known two methods of manufacturing the surgical needle having the proximal end formed therein with the bore.

First one of the two known methods is disclosed in Japanese Patent Application Laid-Open Nos. 52-111294, 60-170590 and 60-184485, Japanese Patent Publication No. 61-58172, Japanese Utility Model Publication No. 56-37918 and Japanese Utility Model Application Laid-Open No. 55-43691, in which a drill or a beam energy is used to form the bore in the proximal end of the surgical needle. It is difficult for the first method, however, to form the small diameter bore correctly along the axis of the needle which is also small in diameter.

The second method is disclosed in Japanese Utility Model Publication No. 28-3184, in which a pipe member is welded to an end face of the proximal end of a needle member. In the second method, since a hollow portion of the pipe member can be used as a bore for attaching a suture, the bore-forming operation like the first method is dispensed with. Further, it is easy for the second method to manufacture a small diameter surgical needle having therein a small diameter bore extending along the axis of the surgical needle. The Japanese utility model does not specifically describe in what manner the pipe member is welded to the proximal end of the needle member. At that time, however, welding has practically been performed in the following manner. That is, the pipe member has been welded to the proximal end of the needle member by means of a so-called butt welding, in which an end face of the pipe member is butted under pressure against an end face of the proximal end of the needle member, and portions of the respective needle and pipe members adjacent the junction therebetween are welded to each other by heat generated due to electric resistance between both the end faces. It is necessary for the butt welding, however, to apply force to the pipe member and the needle member along an axis common to them during the welding operation such that the pipe member and the needle member are urged against each other. Because of such force, melted material tends to be forced out to form flash, so that a step of trimming is required after the welding operation. This trimming operation is troublesome because the surgical needle is very small in diameter, resulting in an increase of the manufacturing cost. Moreover, the melted metal flows under the urging force also into the hollow portion of the pipe member, so that variation occurs in the depths of the bores in the respective surgical needles, which bores are formed respectively by the hollow portions of the pipe members.

Additionally, as the relevant prior art, there is Japanese Patent Application Laid-Open No. 61-45745 corresponding to U.S. Ser. No. 632,343 filed on July 19, 1984, which discloses coloring of surgical needles. In this connection, there is also U.S. Ser. No. 905,521 filed on Sept. 10, 1986 in the name of the same assignee as this application.

Japanese Patent Publication No. 58-39544 and Japanese Patent Application Laid-Open Nos. 49-61980 and 50-119487 disclose a technique in which the suture is drawn out of the surgical needle in order to simplify and facilitate separation between the surgical needle and the suture after the suture has been pierced through a bodily tissue at the surgical operation. Japanese Utility Model Application Laid-Open No. 61-109505 discloses a technique in which a part of the suture adjacent the surgical needle is weakened locally. Furthermore, Japanese Utility Model Application Laid-Open No. 61-109506 discloses a technique in which the suture is connected to the surgical needle by a special connector element.

Japanese Utility Model Publication No. 60-25219 discloses a technique for annealing the proximal end of the surgical needle formed of austenitic stainless steel.

SUMMARY OF THE INVENTION

It is an object of the invention to provide a surgical needle which is easy in manufacturing and is low in production cost.

It is another object of the invention to provide a method of manufacturing the surgical needle.

It is still another object of the invention to provide an apparatus for carrying out the method.

According to the invention, there is provided a surgical needle comprising a needle member, a pipe member arranged at a proximal end of the needle member and a welded portion formed between the needle and pipe members, wherein marks of welding are left as they are on the welded portion so that the welded portion has a surface distinguishable from peripheral surfaces of the respective needle and pipe members.

According to the invention, there is also provided a surgical needle comprising a needle member, a pipe member arranged at a proximal end of the needle member, and a plurality of peripherally spaced welded parts formed at a junction between the needle and pipe members.

According to the invention, there is further provided a method of manufacturing a surgical needle, comprising the steps of: abutting an end face of a pipe member against a proximal end face of a needle member to form an abutting line which is annular in appearance; and supplying a beam energy from beam energy emitting means, toward the abutting line, from a direction substantially perpendicular to the needle and pipe members, thereby welding the needle and pipe members to each other to form a welded portion therebetween.

According to the invention, there is provided an apparatus for manufacturing a surgical needle, comprising:

(a) beam energy emitting means;

(b) rotational support means for supporting a needle member and a pipe member in such a manner that axes of the respective needle and pipe members extend perpendicularly to an axis of a beam energy emitted from the beam energy emitting means and that an end face of the needle member and an end face of the pipe member are abutted against each other at a location coincident with the axis of the laser beam, the rotational support means also rotating the needle and pipe members about their respective axes; and (c) drive means for giving rotation to the rotational support means.

According to the invention, there is also provided an apparatus for manufacturing a surgical needle, comprising a laser beam generating source arranged stationarily, a laser beam emitting section receiving a laser beam from the laser beam generating source through an optical fiber, the laser beam emitting section condensing the laser beam to emit the condensed laser beam, guide means at least including an arcuate portion, moving means for moving the laser beam emitting section along the guide means while maintaining such a posture that an optical axis of the laser beam emitted from the laser beam emitting section passes through a central axis of a radius of curvature of the arcuate portion of the guide means, and support means supporting the needle and pipe members while maintaining them stationary in such a manner that the needle and pipe members are abutted against each other at a location substantially coincident with a plane including the optical axis of the laser beam and that the axes of the respective needle and pipe members are coincident with the central axis of the radius of curvature of the guide means.

According to the invention, there is further provided an apparatus for manufacturing a surgical needle, comprising a laser beam generating source arranged stationarily, dividing means for dividing a laser beam from the laser beam generating source into a plurality of laser beams, a plurality of laser beam emitting sections respectively receiving the laser beams divided by the dividing means, through respective optical fibers, to emit the respective laser beams, and support means for stationarily supporting a needle member and a pipe member in such a manner that the needle and pipe members are abutted against each other at a location substantially coincident with a plane including optical axes of the respective laser beams.

BRIEF DESCRIPTION OF THE DRAWINGS

FIG. 6 is a fragmental enlarged schematic view showing a preferred manner of supplying pulses of a laser beam;

FIG. 7 is a perspective view showing the needle and pipe members tack-welded to each other, before the regular welding is carried out;

FIG. 8 is a schematic plan view showing an example of an annealing manner after completion of welding;

FIG. 9 is a view similar to FIG. 8, but showing another example of the annealing manner;

FIG. 10 is a view similar to FIG. 8, but showing still another example of the annealing manner;

FIG. 11 is a schematic view showing a manner in which only a multiplicity of pipe members are annealed, the annealing being carried out before welding;

FIGS. 12 through 15 are cross-sectional views respectively showing various aspects of the welded portion;

FIGS. 16 and 17 are views showing, in due order, a suture operation carried out by the use of the surgical needle provided with one of the welded portions shown respectively in FIGS. 12 through 15;

FIG. 18 is a view showing another aspect of a surgical needle provided with one of the welded portions illustrated respectively in FIGS. 12 through 15;

FIG. 19 is a top plan view showing an embodiment of an apparatus for carrying out the method according to the invention, an arrangement of respective chuck mechanisms for a needle member and a pipe member and other mechanisms being omitted for clarification;

FIG. 21 is a fragmental plan view of the chuck mechanisms for the respective needle and pipe members employed in the apparatus illustrated in FIG. 19;

FIG. 22 is a front elevational view of the chuck mechanisms illustrated in FIG. 21;

FIG. 23 is an end view of the chuck mechanism for the pipe member, illustrated in FIGS. 21 and 22;

FIG. 24 is an end view of the chuck mechanism for the needle member, illustrated in FIGS. 21 and 22;

FIG. 25 is an enlarged fragmental view of a V-shaped groove illustrated in FIG. 23, the pipe member being set in the V-shaped groove;

FIG. 26 is an enlarged fragmental view of a V-shaped groove illustrated in FIG. 24, the needle member being set in the V-shaped groove;

DETAILED DESCRIPTION

Figure 1:
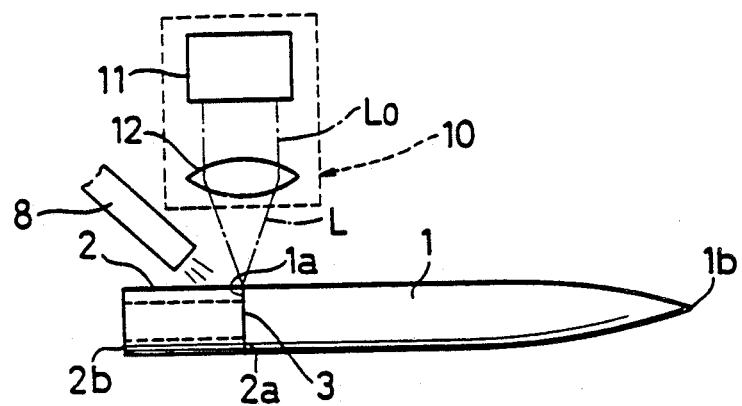
FIG. 1 is a schematic plan view showing an embodiment of a method of welding a needle member and a pipe member to each other, according to the invention.

Referring to FIGS. 1 through 5, there is shown a surgical needle manufacturing method according to an embodiment of the invention. As shown in FIG. 1, a straight needle member 1 and a straight pipe member 2 are first prepared. These needle and pipe members 1 and 2 are formed of austenitic stainless steel having advantages subsequently to be described. The needle member 1 has one end thereof which is formed with a planar end face 1a extending perpendicularly to an axis of the needle member 1. The other end of the needle member 1 is formed into a pointed end 1b. The pipe member 2 is formed in the following manner. That is, a rectangular strip is curled into a tubular form such that one side edge of the strip is abutted against the other side edge.

Then, the one and other side edges are welded to each other to form a tube. Subsequently, the tube is drawn through drawing dies to reduce the diameter of the tube until the diameter is brought to a value equal to the outer diameter of the needle member 1. The diameter-reduced tube is then cut into tube pieces each having a predetermined length. In this manner, the above pipe member 2 is formed by each of the cut tube pieces. The length of the pipe member 2 is substantially equal to the depth of a bore in a surgical needle that is an intended final product. The pipe member 2 is formed at its both ends respectively with planar end faces 2a and 2b extending perpendicularly to the axis of the pipe member 2.

The needle and pipe members 1 and 2 are chucked respectively by a pair of chuck means arranged respectively on a pair of rotary structures independent of each other. The pair of chuck means and the pair of rotary structures are not shown in FIG. 1, but will be described later with reference to FIGS. 19 through 24. When the needle and pipe members 1 and 2 are chucked respectively by the chuck means, one of the planar faces 2a of the pipe member 2 and the planar face 1a of the needle member 1 are abutted against each other such that a single annular line 3 is seen from the outside, which is formed between the respective outer peripheral surfaces of the needle and pipe members 1 and 2.

With the planar faces 1a and 2a abutted against each other, the needle and pipe members 1 and 2 are welded to each other by a laser beam L emitted from a laser beam emitting unit 10. The laser beam emitting unit 10 comprises, as its principal components, a generating source 11 of a collimated laser beam Lo, and a condenser optical system 12 including a convex lens for condensing the collimated laser beam Lo emitted from the generation source 11, onto peripheral surfaces of portions of the respective needle and pipe members 1 and 2 adjacent the above-mentioned abutting line 3.

Figure 2:
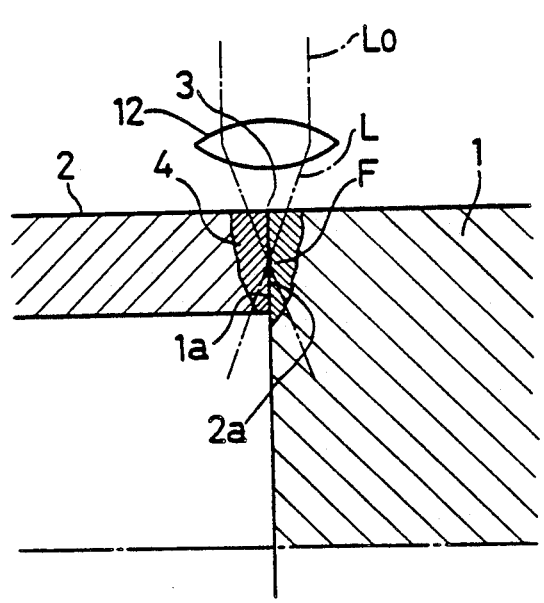
FIG. 2 is a fragmental enlarged cross-sectional view showing the welded portion obtained by the welding method illustrated in FIG. 1.

It is shown in FIG. 2 that a region on the peripheral surface of the needle member 1, which is supplied with the condensed laser beam L, is substantially equal in area to that on the peripheral surface of the pipe member 2, which is supplied with the condensed laser beam L. However, the laser receiving region on the needle member 1 may be larger in area than that on the pipe member 2, in consideration of the fact that the needle member 1 is larger in heat capacity than the pipe member 2.

Figure 4:
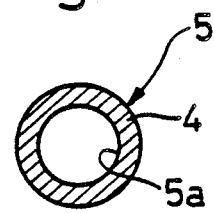
FIG. 4 is a cross-sectional view showing the welded portion of the surgical needle illustrated in FIG. 3.
Figure 3:
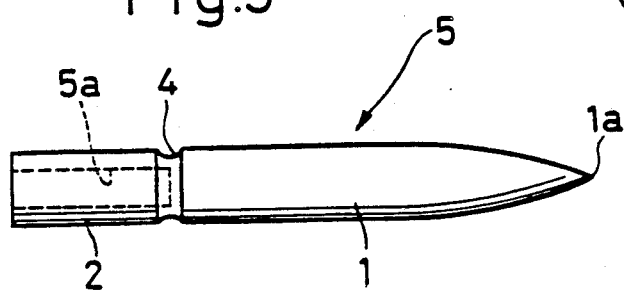
FIG. 3 is a plan view of a surgical needle after completion of welding in accordance with the method illustrated in FIG. 1.

By application of the laser beam L, portions of the respective needle and pipe members 1 and 2, which are adjacent the respective end faces 1a and 2a abutted against each other, are melted. After melting, the melted portions are cooled and solidified, thereby completing connection or welding between the needle and pipe members 1 and 2. The welding due to the laser beam L is carried out only at a single location on the abutting line 3, if the needle and pipe members 1 and 2 are stationary. In the illustrated embodiment, therefore, with the needle and pipe members 1 and 2 maintained abutted against each other, pulses of the laser beam L are successively applied to the abutting line 3 at intervals of a short period of time, while rotating the rotary structures respectively supporting the needle and pipe members 1 and 2 at the same rotational speed, thereby successively carrying out welding along the entire circumferential length of the abutting line 3. As a result, as shown in FIGS. 3 and 4, a straight surgical needle 5 is formed, which is provided with an annular welded portion 4 and which is formed with a bore 5a.

Figure 5:
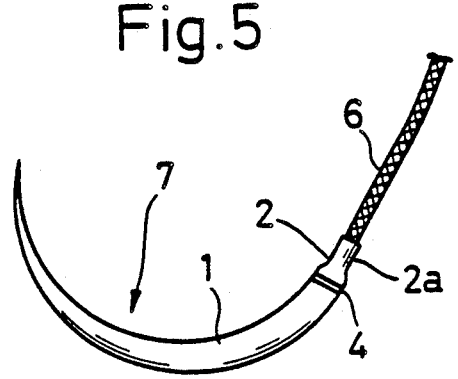
FIG. 5 is a view showing the surgical needle which is bent into a curved form and to which a suture is attached, after completion of welding.

The surgical needle 5 provided with the bore 5a is bent into a curved form by a known bending device as disclosed in Japanese Patent Publication No. 60-18256. Further, with an end of a suture inserted into the bore 5a, the proximal end of the surgical needle 5 is staked by a staking device disclosed in U.S. Pat. No. 4,722,384 or the like. As a consequence, there is provided a curved surgical needle 7 having attached thereto a suture 6, that is a final product as shown in FIG. 5.

In the welding described above, the energy of the laser beam L per one pulse, the time interval between each pair of adjacent pulses, a focal position F (see FIG. 2) and the like are adjusted in such a manner that the penetration depth of the welded portion 4 is substantially consistent with the radial wall thickness of the pipe member 2. Additionally, as shown in FIG. 2, if the focal position F of the condenser optical system 12 is located substantially at the radial center or the vicinity thereof, of the radial wall thickness of the pipe member 2, the consumptive energy of the laser beam L can be reduced.

Since the laser beam L can supply energy of a controlled amount to the junction between the needle and pipe members 1 and 2, it is possible to carry out welding along the entire circumferential length of the abutting line 3 substantially uniformly, that is, with a constant weld penetration depth.

It is unnecessary for the welding due to the laser beam to apply force to the needle and pipe members 1 and 2 toward each other to thereby press them against each other. It is mere necessary to maintain the needle and pipe members 1 and 2 abutted against each other. Accordingly, an amount by which the melted metal penetrates into the cavity within the pipe member 2, is extremely small, as compared with the electric resistance welding. Therefore, the cavity within the pipe member 2 remains substantially unchanged as the bore 5a for attaching the suture 6, making it possible to maintain the depth of the bore 5a constant.

Moreover, since the above-mentioned urging force is not applied to the needle and pipe members 1 and 2, no flash occurs which projects outwardly. Rather, due to the facts that minute spaces are formed between the abutted end faces 1a and 2a of the respective needle and pipe members 1 and 2 by minute irregularities on the end faces 1a and 2a and by minute dust interposed between the end faces 1a and 2a, and are filled with a part of the melted metal, and that a part of the melted metal is slightly drawn toward the cavity within the pipe member 2 when the melted metal is cooled, the welded portion 4 caves in from the outer peripheral surfaces of the respective needle and pipe members 1 and 2 by few micron meters or to the extent slightly more than few micron meters, as shown in FIG. 3. The caving-in amount is exaggeratedly shown in FIG. 3. As a result, it is possible for the invention to dispense with the trimming step.

Since the marks of welding are left on the surface of the above-mentioned annular welded portion 4, as shown in FIG. 5, it is possible to distinguish, in appearance, the welded portion 4 from the peripheral surfaces of the respective needle and pipe members 1 and 2. There are two aspects of the surface of the welded portion 4.

The first aspect of the surface of the welded portion 4 is obtained in the following manner. That is, as shown in FIG. 1, inert gas such as argon gas, nitrogen gas or the like is blown at slow speed from a pipe 8 extremely small in diameter, against a region on the peripheral surfaces of the respective needle and pipe members 1 and 2, to which region the laser beam L is applied. By doing so, the surface of the welded part 4 is prevented from being oxidized and is formed into a mirror surface, so that the surface of the welded portion 4 glistens as compared with the surfaces of the respective needle and pipe members 1 and 2. Moreover, when the welding is carried out in a vacuum, the surface of the welded portion 4 is likewise formed into a mirror surface.

The second aspect of the surface of the welded portion 4 is obtained in such a manner that welding is carried out in the atmosphere without the inert gas being blown against the surfaces of the respective needle and pipe members 1 and 2. In this case, an oxide film is formed on the surface of the welded portion 4, so that the surface of the welded portion 4 is distinguished from the peripheral surfaces of the respective needle and pipe members 1 and 2.

The surface of the welded portion 4 cannot be vanished by electrolytic polishing or chemical polishing, unless the surface is mechanically ground or polished.

The ring-like welded portion 4 serves as a mark when, for example, the pipe member 2 is staked, so that it can be ensured that a part (designated by the character 2a in FIG. 5) of the pipe member 2 spaced a predetermined distance from the welded portion 4 is staked. This makes it possible to prevent occurrence of cracks or the like in the pipe member 2 due to staking of the welded portion 4 or a part very close thereto. Moreover, the ring-like welded portion 4 serves also as a mark by which when a doctor clamps the surgical needle with a chuck jig at a surgical operation, he can clamp the surgical needle while keeping away from the pipe member 2 which is low in strength.

It is preferable that pulses of the laser beam, L are applied in a manner as shown in FIG. 6. In FIG. 6, a region of melting occurring due to a single pulse of the laser beam L is indicated by a circle C. The pulses of the laser beam L are successively outputted at intervals of a short period of time. Since the needle and pipe members 1 and 2 are rotated about their respective axes simultaneously with the output of the pulses, the pulses are successively applied to the needle and pipe members 1 and 2 along the abutting line 3 at narrow angular intervals. Thus, welded parts produced by the respective pulses are overlapped with each other. Since a part of the needle and pipe members 1 and 2, to which a first one of the pulses of the laser beam L is to be applied, is at the room temperature and is cool, an amount of melting at the part is small when the laser beam L is applied to the part. Accordingly, the region of melting appearing on the surface is narrow, and the depth of penetration is shallow. The depth of penetration does not reach a position corresponding to the radial wall thickness of the pipe member 2, but occupies only the outer surface layer. Thus, the welding is incomplete. A second pulse of the laser beam L is applied to a second part immediately adjacent the part to which the first pulse is applied, at an interval of an extremely short period of time. Since the second part is raised in temperature by the first pulse, the second part increases in amount of melting when the second pulse is applied to the second part, so that depth of penetration increases. At a part to which a pulse of the laser beam L subsequent to several pulses is applied, as shown in FIG. 2, the depth of penetration of the welded portion 4 is substantially equal to the radial wall thickness of the pipe member 2, so that the welded portion 4 is locally brought to a complete welded form. Accordingly, if it is desired to carry out the complete welding along the entire circumferential length of the abutting line 3, in other words, if it is desired that welding is carried out over the entire region of the end face 2a of the pipe member 2, as shown in FIG. 6, the pulses of the laser beam L are again applied along the abutting line 3 by a predetermined length from the part to which the first pulse is applied.

The energy of the laser beam L may be weak at the initial few pulses. In this case, the energy of the laser beam L is gradually raised to a steady energy level. By doing so, the length of the initial incomplete welded part along the abutting line 3 is increased, thereby obtaining a tack-welding effect. The tack-welding effect will be described later in detail with reference to FIG. 7 which remarkably shows the tack-welding.

Moreover, the pulses of the laser beam L may be applied through a predetermined length from the END position shown in FIG. 6, while gradually weakening the energy of the laser beam L. By doing so, it is possible to prevent a mark, like a crater, of the last pulse of the laser beam L from being left on the welded portion 4.

By the way, when the laser beam L is applied to the junction between the needle and pipe members 1 and 2 to successively carry out welding along the abutting line 3, a bending force acts to the needle and pipe members 1 and 2 at the initial stage of the welding step. The bending force tends to angularly move the needle and pipe members 1 and 2 about the part at which welding has already been completed, so that the needle and pipe members 1 and 2 are brought into misalignment with each other. If the needle and pipe members 1 and 2 are chucked respectively by a pair of chucks at respective positions remote from the abutting line 3, the needle and pipe members 1 and 2 are subject to the bad influence of the bending force, so that there may be a case where the needle and pipe members 1 and 2 are welded to each other while being maintained misaligned. This deficiency can be dissolved in the following manner. That is, prior to the regular welding, as shown in FIG. 7, a single short pulse of the laser beam is applied to each of a plurality of, for example, three or more locations on the abutting line 3, which are equidistantly spaced circumferentially from each other. Since the pulses of the laser beam are supplied respectively to the locations on the abutting line 3 under the condition that the needle and pipe members 1 and 2 are at the room temperature and are cool, the depth of penetration of each of welded parts 4' is shallow. Accordingly, substantially no bending force is produced due to the welded parts 4'. When the regular welding is carried out as shown in FIG. 6 with the needle and pipe members 1 and 2 tack-welded to each other, even if a bending force occurs temporarily due to the regular welding, the tack-welded parts 4' serve as resistance to the bending force. Thus, welding can be effected without the needle and pipe members 1 and 2 being brought into misalignment with each other.

Since the austenitic stainless steel is used as the material of the needle and pipe members 1 and 2, the surgical needle 7 is excellent in corrosion resistance. Moreover, welding due to the laser beam L is accompanied with local rapid heating and rapid cooling. However, the austenitic stainless steel is not hardened by the rapid cooling, but is softened. Therefore, it is possible to prevent occurrence of cracks in the vicinity of the welded portion 4 due to the hardening by the rapid cooling during welding.

The welded portion 4 is soft as compared with the needle and pipe members 1 and 2. Accordingly, when a bending force is applied to the surgical needle 7, the needle 7 is bent at an acute angle at the welded part 4, so that there may be a case where cracks occur in the welded portion 4 or the welded portion 4 is damaged. In view of this, when welding has been completed, as shown in FIG. 8, either one of the laser beam emitting unit 10 and the needle and pipe members 1 and 2 is moved in a direction perpendicular to the aligned axes of the respective needle and pipe members 1 and 2, thereby moving the peripheral surfaces of the respective needle and pipe members 1 and 2, away from the focal position, that is, away from the laser beam emitting unit 10. Under this condition, if the laser beam L is applied to the needle and pipe members 1 and 2 while rotating them, the spot area to which the laser beam L is applied is larger than that during the welding. By this reason, a region designated by the reference numeral 9 in FIG. 8, which is wider than the welded portion 4 and which extends along the welded portion 4, is annealed at a temperature lower than the welding temperature and is softened. Thus, when a bending force is applied to the surgical needle 7, deformation occurs not only in the welded portion 4, but also in the annealing region 9, so that the surgical needle 7 is bent as a whole into a curved form. Accordingly, it can be ensured to prevent occurrence of cracks in the welded portion 4 and destruction thereof.

Further, after annealing at the region 9 has been completed, the chuck is removed from the pipe member 2, and the rotary structure supporting the needle member 1 is moved axially thereof or in a direction indicated by the arrow in FIG. 8 while the needle member 1 is maintained chucked. At the same time, the needle and pipe members 1 and 2 are rotated about their respective axes, thereby enabling the entire length of the pipe member 2 to be annealed by the laser beam L. This makes it possible to prevent cracks from occurring when the pipe member 2 is staked to attach the suture to the surgical needle 7, and also makes it possible to increase the attaching strength of the suture. The end of the pipe member 2 on the side opposite to the welded portion 4 may not necessarily be softened.

Moreover, annealing may be carried out as shown in FIG. 9. That is, by moving the needle and pipe members 1 and 2, or by moving the laser beam emitting unit 10, the peripheral surfaces of the needle and pipe members 1 and 2 are moved to a position closer to the laser beam emitting unit 10 than the focal position, so that the spot area increases to which the laser beam L is applied. Other arrangement of the embodiment shown in FIG. 9 is the same as that shown in FIG. 8.

Furthermore, annealing may be effected as shown in FIG. 10. That is, after welding, a flame of a burner 10A is used to anneal the vicinity of the welded portion 4 and the pipe member 2.

Further, annealing may be performed as shown in FIG. 11. That is, prior to welding, a multiplicity of pipe members are wrapped up in a stainless steel foil 15. The pipe members wrapped up in the foil 15 are gotten into an electric furnace 10B and are heated thereby. Alternatively, the pipe members wrapped up in the foil 15 are heated from the outside by the burner shown in FIG. 10. In this manner, only the pipe members are annealed together. The volume of the multiplicity of pipe members is extremely small. For example, the volume of ten thousand pipe members is only 1 cm$^3$. Accordingly, the annealing method illustrated in FIG. 11 makes it possible to uniformly and inexpensively anneal a large quantity of pipe members for a short period of time without the pipe members being oxidized.

Welding due to the laser beam may be carried out partially with respect only to a portion or portions of the entire region of the end face of the pipe member 2. For example, the welding may be carried out along the entire circumferential length of the abutting line 3 in such a manner that the depth of penetration is shallower than the radial wall thickness of the pipe member 2. Moreover, the welding may be carried out with respect only to a predetermined angular extent or extents along the abutting line 3.

In each of embodiments shown respectively in FIGS. 12 through 15, welding is carried out with respect only to predetermined angular extents along the abutting line 3, in order to enable a surgical needle to have an especial function. The needle member 1 is bent into a curved form after or before welding. In FIGS. 12 through 15, the inside of the curved form is designated by the character "I", while the outside of the curved form is designated by the character "O", in order to facilitate explanation of welded positions.

In the embodiment illustrated in FIG. 12, no laser beam is applied to both the inside "I" and the outside "O" so that two welded parts 4 and 4 are formed by the laser beam. The two welded parts 4 and 4 are angularly displaced by 90 degrees from the inside "I" and the outside "O". Each welded part 4 has an angular extent of the order of 70 to 80 degrees, and has the depth of penetration of the order of a third or a fourth of the radial wall thickness of the pipe member 2.

In the embodiment illustrated in FIG. 13, two welded parts 4 and 4 are formed respectively in relatively narrow angular extents. The two welded parts 4 and 4 are angularly displaced by 90 degrees from the inside "I" and the outside "O". The depth of penetration of each welded part 4 is substantially equal to the radial wall thickness of the pipe member 2.

In the embodiment illustrated in FIG. 14, except for the outside "O" of the curved form, three welded parts 4 are formed respectively at three locations circumferentially equidistantly spaced from each other. Each of the welded parts 4 has an angular extent which is relatively small, and has the depth of penetration substantially equal to the radial wall thickness of the pipe member 2.

In the embodiment illustrated in FIG. 15, four welded parts 4 are formed. Two of the four welded parts 4 are angularly displaced by 45 degrees from the inside "I", and the remaining two parts 4 are angularly displaced by 45 degrees from the outside "O". Each welded part 4 has a relatively small angular extent, and has the depth of penetration substantially equal to the radial wall thickness of the pipe member 2.

For the surgical needle provided with the welded parts 4 in one of the embodiments illustrated respectively in FIGS. 12 through 15, it is possible to maintain the tension strength in the direction along the aligned axes of the respective needle and pipe members 1 and 2 at a sufficient level. However, the welded parts 4 are weak in bending strength. Such characteristic is positively utilized, thereby enabling the following operational manner to be adopted. That is, a doctor first clamps a portion of the surgical needle 7 adjacent the proximal end thereof, by means of a chuck jig 18. Only a clamping section of the chuck jig 18 is shown in FIG. 16. The surgical needle 7 is pierced through two parts of the bodily tissue cut by a bistoury. Then, the chuck jig 18 is once removed from the surgical needle 7, and again clamps a portion of the surgical needle 7 adjacent a distal end thereof. As shown in FIG. 17, with the axis of the pipe member 2 substantially aligned with the suture 6, the surgical needle 7 is pulled until the opposite end portions of the suture 6 coming out of the bodily tissue are brought to their respective desired lengths. Subsequently, as shown in FIG. 17, the surgical needle 7 is angularly moved through 90 degrees about a point at which the suture 6 is connected to the pipe member 2, such that the axis of the pipe member 2 is substantially perpendicular to the suture 6. Under such condition, the doctor clamps the suture 6 with fingers 19 of his hand which is not holding the chuck jig 18. Then, the doctor pulls the surgical needle 7 in the direction indicated by the arrow in FIG. 17. By doing so, a bending stress is applied to the welded parts 4 to destroy the same, whereby the surgical needle 7 is disassembled into the needle member 1 and the pipe member 2 having attached thereto the suture 6. Thus, the operation of cutting the suture 6 prior to the operation of tying the suture 6 can be dispensed with, making it possible to enhance the operability at the surgical operation.

It is to be noted here that, in each of the embodiments illustrated respectively in FIGS. 12 through 15, the tension force applied to the suture 6 acts such that one of non-welded portions is brought to the tension side. By doing so, the pipe member 2 tends to be angularly moved about the non-welded portion, so that destruction of the welded parts 4 is facilitated due to the principles of the lever. In the actual suture operation, the doctor's hand holding the chuck jig 18 is twisted unnaturally in the state indicated by the phantom lines in FIG. 17. When the surgical needle 7 is angularly moved through 90 degrees about the point at which the suture 6 is connected to the pipe member 2, that is, when the surgical needle 7 is angularly moved to the position indicated by the solid lines in FIG. 17, the doctor's hand is in the natural state. Accordingly, it is convenient that the outside "O" of the curved form is brought to the tension side. To this end, it is preferable that the outside "O" is brought to the non-welded part, as shown in FIGS. 12 through 15.

In order to show that the surgical needle can be applied to the special suture operational method as described above, the peripheral surface of the pipe member 2 may be colored by an oxidizing treatment or a plating treatment which can be carried out after or before welding due to the laser beam. Moreover, only a portion of the peripheral surface of the pipe member 2, which is located on the outside "O" of the curved form and which is the non-welded part, may be colored in order to indicate the pulling direction.

The needle member 1 and the pipe member 2 may be the same in material as each other, or may be different in material from each other. It is required for the needle member 1 to use material work-hardened in order to enhance the ability of piercing into the bodily tissue. However, the material of the pipe member 2 may have or may not have the work-hardening ability. For example, the needle member 1 employs stainless steel of one of types SUS 302, 304 and 631 which are work-hardened. On the other hand, the pipe member 2 may use, for example, stainless steel of type SUS 316 which is not work-hardened, in addition to the same material as the needle member 1.

The pipe member 2 may have its outer diameter smaller than that of the needle member 1. Moreover, such a pipe member may be employed that an outer diameter of one end of the pipe member to be abutted against the end face of the needle member is substantially equal to the outer diameter of the needle member, and the other end of the pipe member is enlarged in diameter into a trumpet form. Alternatively, an annular step may be formed to enlarge the other end of the pipe member. The end of the suture is inserted into the enlarged other end of the pipe member and, subsequently, the enlarged other end is staked. Accordingly, the other end of the pipe member is finally brought to an outer diameter equal to or smaller than the abutting one end of the pipe member. Prior to welding, processing or working may be applied to the inner peripheral surface of the pipe member to form threads or irregularities for enhancing the attaching strength of the suture.

The pipe member having a considerable length may be welded to the needle member. In this case, after the welding, the long pipe member is cut at a location spaced a desired distance from the welded portion.

The laser beam may be applied to the junction between the needle and pipe members continuously, in place of the pulses.

An electron beam may be utilized in substitution for the laser beam. When the electron beam is employed, the beam is condensed or concentrated by an electromagnetic lens. Moreover, it is preferable that welding due to the electron beam is carried out in a vacuum.

The needle and pipe members may be welded to each other with a slight gap intentionally left between them.

Prior to welding of the needle and pipe members to each other, the needle member may beforehand be bent into a curved form. Alternatively, a portion of the pipe member, into which the end of the suture has been inserted, may beforehand be staked.

An apparatus suitable for carrying out the method described with reference to FIGS. 1 through 6 and 8 will next be described with reference to FIGS. 19 through 29.

Figure 20:
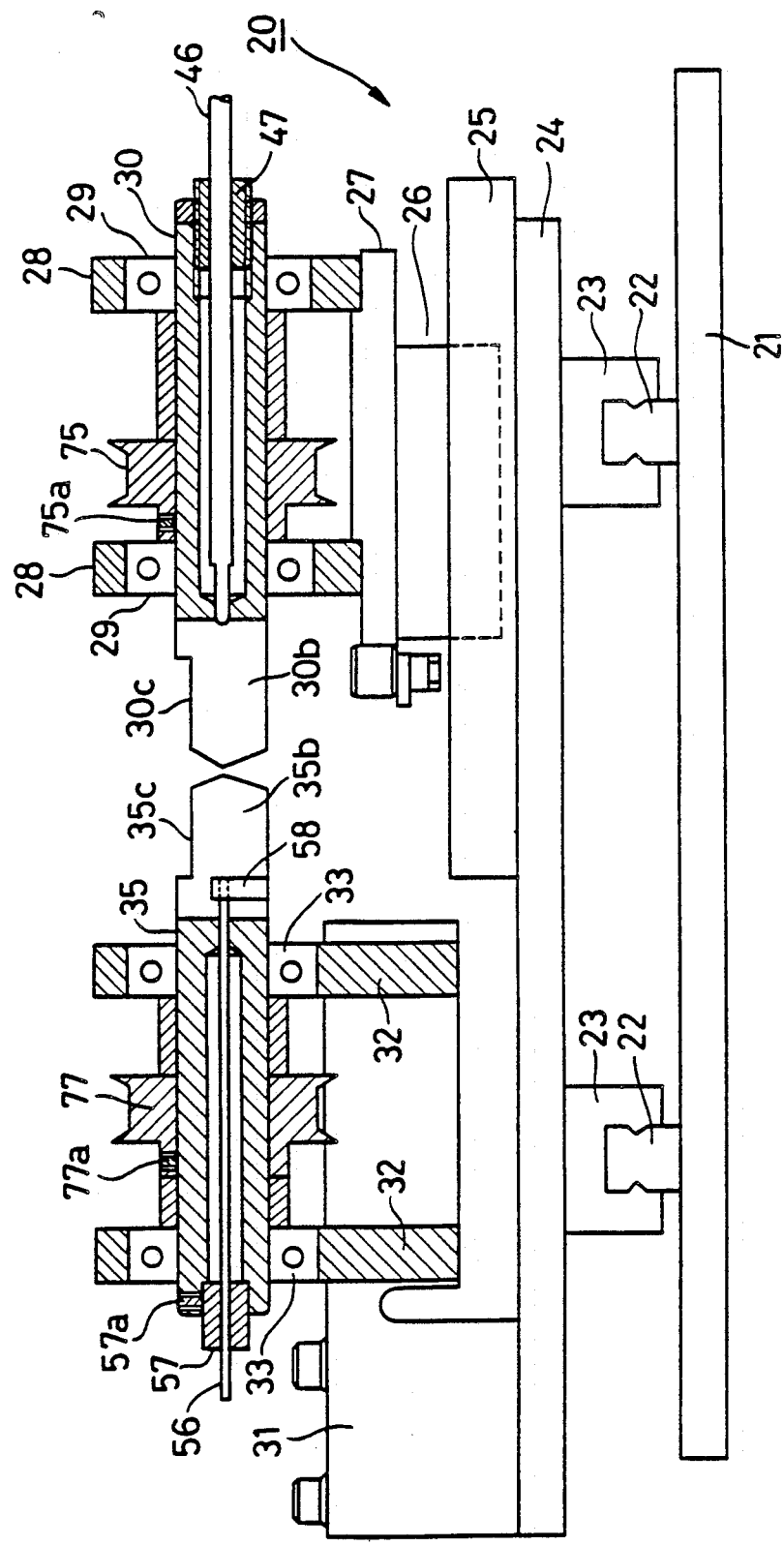
FIG. 20 is a cross-sectional view taken along line XX—XX in FIG. 19.

FIG. 19 is a plan view of an apparatus 20 having a function of supporting the needle and pipe members 1 and 2 while rotating them. The apparatus 20 comprises a base plate 21 which is fixedly mounted to a bed (not shown). The laser beam emitting unit shown in FIG. 1 is mounted on the bed at a location adjacent the base plate 21, that is, at an upper location as viewed in FIG. 19. The laser beam emitting unit is designed to horizontally emit the laser beam whose optical axis is designated by the character A in FIG. 19. As best shown in FIG. 20, a pair of rails 22 and 22 extending parallel to the optical axis A of the laser beam are fixedly mounted to the upper surface of the base plate 21. A pair of sliders 23 and 23 are fixedly mounted to a lower surface of a first moving plate 24, and are fitted respectively about the rails 22 for sliding movement therealong. Thus, the first moving plate 24 is movable in the direction along the optical axis A of the laser beam. A rail 25 is fixedly mounted to the upper surface of the first moving plate 24, and extends in a direction perpendicular to the rails 22. A slider 26 is fixedly mounted to a lower surface of a second moving plate 27, and is fitted into the rail 25 for sliding movement therealong. Thus, the second moving plate 27 is movable in a direction perpendicular to the optical axis A of the laser beam.

A pair of brackets 28 and 28 are fixedly mounted to the upper surface of the second moving plate 27. A first hollow spindle 30 is rotatably supported by a pair of bearings 29 and 29 mounted respectively in the brackets 28 and 28. The first spindle 30 has an axis intersected at right angles with the optical axis A of the laser beam.

On the other hand, an upstanding bracket 31 is fixedly mounted to the upper surface of the first moving plate 24. A pair of brackets 32 and 32 are fixedly mounted to a side face of the bracket 31. A second hollow spindle 35 is rotatably supported by a pair of bearings 33 and 33 mounted respectively in the brackets 32 and 32. The second spindle 35 has an axis aligned with the axis of the first spindle 30.

Confronting forward ends 30a and 35a of the respective first and second spindles 30 and 35 are cut out such that each of the forward ends 30a and 35a has a cross-sectional shape near a semi-circular shape, as shown in FIGS. 23 and 24. The forward ends 30a and 35a have their respective planar faces 30b and 35b displaced from the axes of the respective spindles 30 and 35, and respective planar faces 30c and 35c extending perpendicularly to the respective planar faces 30b and 35b.

As shown in FIGS. 21, 22 and 24, a first chuck mechanism 40 for supporting the needle member 1 is mounted to the first spindle 30. The first chuck mechanism 40 has a support member 41 which is supported on the planar face 30b of the first spindle 30 by an L-shaped bracket 42 and which is fixed by screws 42a. The support member 41 is formed therein with a V-shaped groove 41a shown in FIG. 24 and in FIG. 26 on an enlarged scale. The previously mentioned straight needle member 1 can be set in the V-shaped groove 41a. With the needle member 1 set in the V-shaped groove 41a, the axis of the needle member 1 is aligned with the axis of the first spindle 30.

The first chuck mechanism 40 further has a retainer member 43 which is supported on the planar face 30b of the first spindle 30 by means of a pin 43a for pivotal movement about an axis of the pin 43a. On the other hand, an L-shaped leaf spring 44 (see FIG. 21) is fixed to the planar face 30c by a screw 44a. Biasing force of the leaf spring 44 is applied to the retainer member 43 through a screw 44b threadedly engaged with the forward end of the leaf spring 44. Thus, the forward end 43b of the retainer member 43 can retain the needle member 1 set in the V-shaped groove 41a.

A relatively weak auxiliary leaf spring 45 is fixed by a screw 45a to a face of the retainer member 43 on the side of the support member 41, and can lightly retain the needle member 1 set in the V-shaped groove 41a.

A chuck releasing pin 46 extends through the first spindle 30. When a forward end of the chuck releasing pin 46 pushes the rearward end 43c of the retainer member 43, the retainer member 43 is pivotally moved about the axis of the pin 43a in the clockwise direction as viewed in FIG. 22 so that the forward end 43b of the retainer member 43 is moved away from the needle member 1, thereby releasing the needle member 1 from the chucked state. As shown in FIG. 19, a support member 47 is screwed into the proximal end of the first spindle 30. The chuck releasing pin 46 slidably extends through the support member 47 and projects therefrom outwardly.

As shown in FIGS. 21 through 23, a second chuck mechanism 50 for supporting the pipe member 2 is mounted to the second spindle 35. The second chuck mechanism 50 has a support member 51 which is supported on the planar face 35b of the second spindle 35 by an L-shaped bracket 52 and which is fixed by screws 52a. The support member 51 is formed therein with a V-shaped groove 51a shown in FIGS. 23 and 25, in which the straight pipe member 2 can be set. With the pipe member 2 set in the V-shaped groove 51a, the axis of the pipe member 2 is aligned with the axis of the second spindle 35.

The second chuck mechanism 50 further has a retainer member 53 which is supported on the planar face 35b of the second spindle 35 by a pin 53a for pivotal movement about an axis of the pin 53a. On the other hand, an L-shaped leaf spring 54 (see FIG. 21) is fixed to the planar face 35c by a screw 54a. Biasing force of the leaf spring 54 is applied to the retainer member 53 through a screw 54b threadedly engaged with a forward end of the leaf spring 54, whereby a face 53b of the retainer member 53 can retain the pipe member 2 set in the V-shaped groove 51a.

As shown in FIG. 20, a pusher 56 having an axis aligned with the V-shaped groove 51a in the support member 51 extends through the second spindle 35. A proximal end of the pusher 56 slidably extends through a support member 57 fixed to the proximal end of the second spindle 35 by a set screw 57a, and projects outwardly from the support member 57. The forward end of the pusher 56 is slidably supported by a support member 58 which is fixed to the planar face 35b of the second spindle 35 by means of screws 58a.

Figure 27:
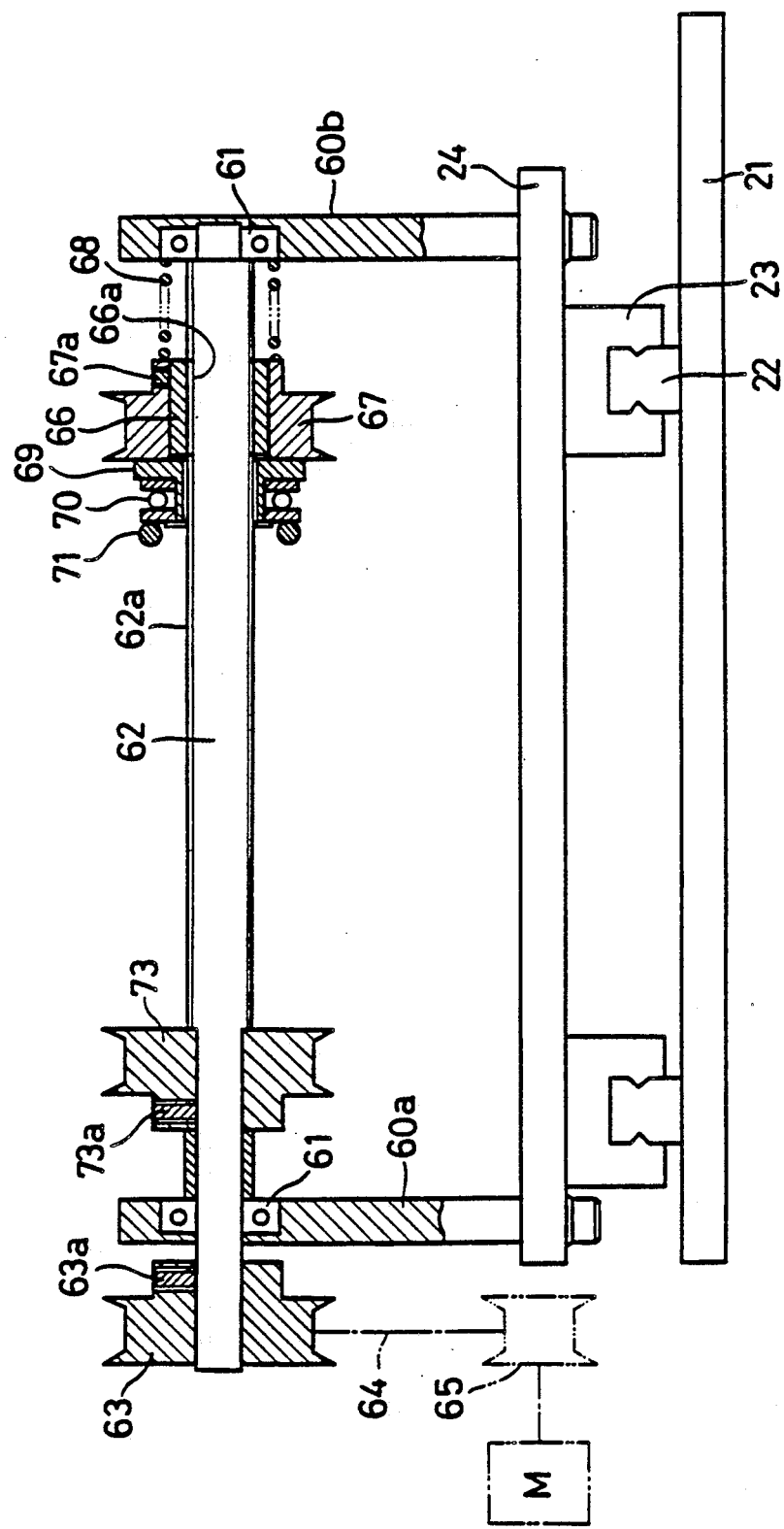
FIG. 27 is a cross-sectional view taken along line XXVII—XXVII in FIG. 19.

As shown in FIGS. 19 and 27, a pair of brackets 60a and 60b are fixedly mounted to the upper surface of the first moving plate 24. A synchronous shaft 62 parallel to the spindles 30 and 35 is rotatably supported by a pair of bearings 61 and 61 mounted respectively in the brackets 60a and 60b. The synchronous shaft 62 has one end thereof to which a pulley 63 is fixedly mounted by a set screw 63a. The pulley 63 is drivingly connected to a motor M fixedly mounted to the aforesaid bed (not shown), through a timing belt 64 and a pulley 65.

A spline 62a is formed on an axial portion of the peripheral surface of the synchronous shaft 62, which extends over a predetermined length. A sleeve 66 having an inner peripheral surface formed with a spline 66a is mounted on the synchronous shaft 62 for sliding movement therealong in such a manner that the spline 66a on the sleeve 66 is in engagement with the spline 62a on the synchronous shaft 62. A pulley 67 is fitted about the sleeve 66 and is fixed thereto by means of a set screw 67a. The pulley 67 and the sleeve 68 are biased by a spring 68 in the left-hand direction as viewed in FIGS. 19 and 27. A tube 69 having an end flange is fixed to an end face of the pulley 67 on the side opposite to the spring 68. A bearing 70 is mounted about the tube 69. Movement of the pulley 67 and the sleeve 66 to the left-hand direction is restricted by a bifurcated fork 71 which is fixedly mounted to the second moving plate 27.

On the other hand, a third pulley 73 is mounted on a portion of the synchronous shaft 62 which is not formed with the spline 62a. The third pulley 73 is fixed to the synchronous shaft 62 by a set screw 73a.

As shown in FIGS. 19 and 20, a pulley 75 is fixedly mounted to the first spindle 30 by a set screw 75a, at a location corresponding to the pulley 67 on the synchronous shaft 62. The pulleys 67 and 75 are connected to each other through a timing belt 76. As will be described later, with movement of the second moving plate 27, the first spindle 30 as well as the pulley 75 move. At this time, the fork 71 fixedly mounted to the second moving plate 27 pushes the pulley 67 to move the same. Accordingly, the relative positional relationship between the pulleys 67 and 75 is maintained unchanged, making it possible to satisfactorily secure rotative transmission through the timing belt 76.

On the other hand, a pulley 77 is fixedly mounted to the second spindle 35 by a set screw 77a, at a location corresponding to the pulley 73 on the synchronous shaft 62. The pulleys 73 and 77 are connected to each other through a timing belt 78. The pulleys 67, 73, 75 and 77 are equal in diameter to each other. Accordingly, when the synchronous shaft 62 is rotated by the motor M, the first and second spindles 30 and 35 are rotated at the same rotational speed while the relative angular positional relationship between the first and second spindles 30 and 35 is maintained unchanged.

Figure 28:
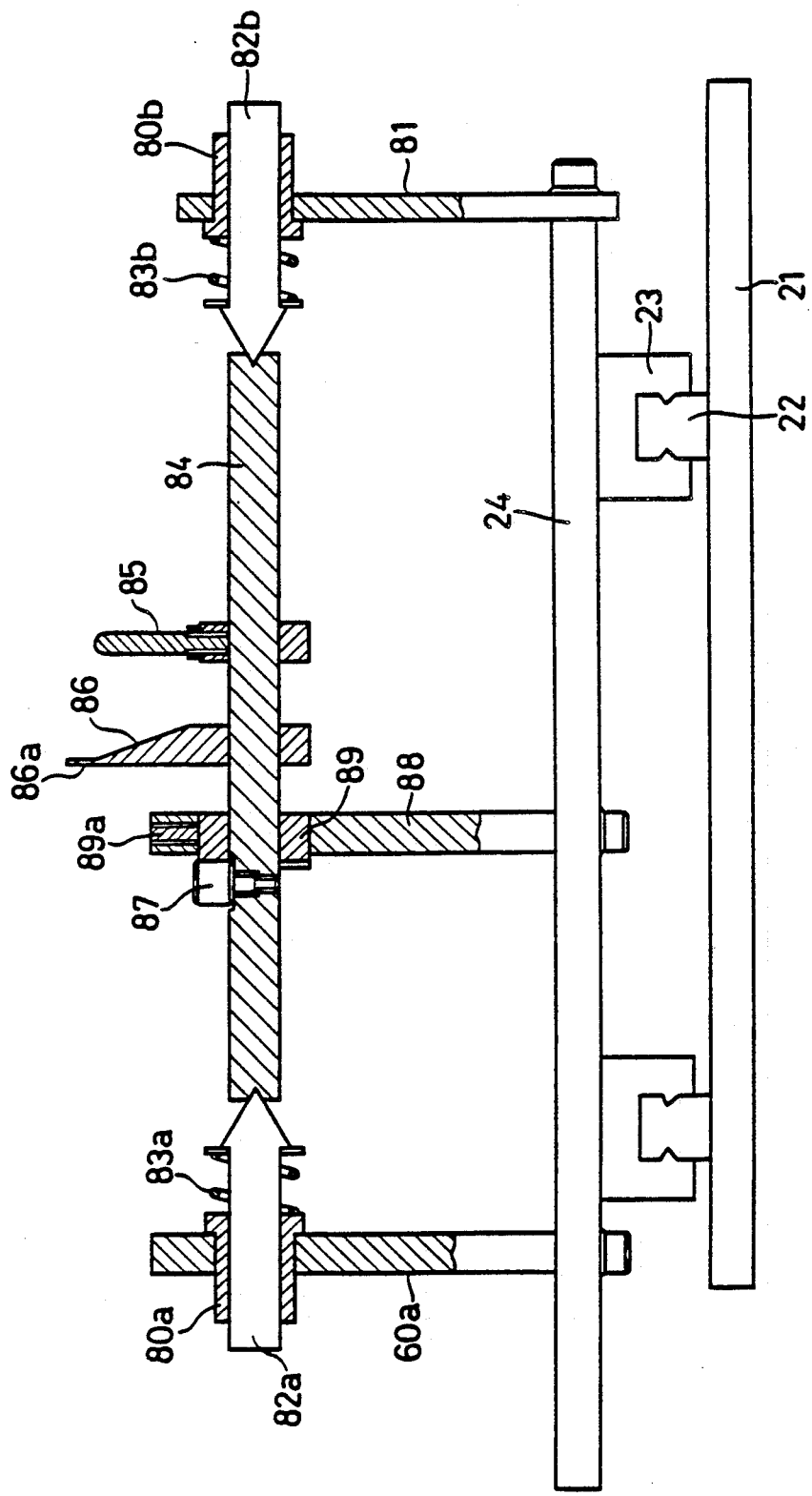
FIG. 28 is a cross-sectional view taken along line XXVIII—XXVIII in FIG. 19.

As shown in FIGS. 19 and 28, a sleeve 80a is fixedly mounted to the aforesaid bracket 60a. A bracket 81 is fixedly mounted to the first moving plate 24 at a location spaced away from the bracket 60a in the direction perpendicular to the optical axis A of the laser beam. Another sleeve 80b is fixedly mounted to the bracket 81. A pair of center shafts 82a and 82b are supported respectively by the sleeves 80a and 80b for sliding movement therealong such that axes of the respective center shafts 82a and 82b are aligned with each other. The center shafts 82a and 82b have their respective pointed ends, and are biased toward each other respectively by springs 83a and 83b. A positioning shaft 84 is supported between and by the pointed ends of the respective center shafts 82a and 82b for angular movement about an axis of the positioning shaft 84. An operating lever 85 is mounted on the shaft 84 for angular movement therewith. A positioning lever 86 is also mounted on the shaft 84 for angular movement therewith. In FIG. 28, the positioning lever 86 and the operating lever 85 are shown as having their respective attaching angles equal to each other, in order to facilitate understanding of the construction. In practice, however, the positioning lever 86 and the operating lever 85 are angularly displaced in attaching angle from each other by 90 degrees, as shown in FIG. 19. A cam follower 87 is rotatably mounted on the shaft 84. On the other hand, a bracket 88 is fixedly mounted to the first moving plate 24. A face cam 89 is fixed to the bracket 88 by a set screw 89a. The shaft 84 extends through the center of the face cam 89. The cam follower 87 is abutted against a cam face of the face cam 89.

Normally, as shown in FIG. 19, the positioning lever 86 is in a vertically upstanding position, while the operating lever 85 is in a horizontal position. When the operating lever 85 is angularly moved about the axis of the shaft 84 by 90 degrees to a vertically upstanding position, the positioning lever 86 is angularly moved to a horizontal position facing toward the spindles 30 and 35. During this angular movement, the cam action between the face cam 89 and the cam follower 87 causes the positioning lever 86 to be moved in the left-hand direction as viewed in FIGS. 19 and 28, while the positioning lever 86 is angularly moved such that a positioning face 86a at the forward end of the positioning lever 86 approaches the forward end of the second spindle 35. Finally, the positioning face 86a is brought to a position coincident with a vertical plane including the optical axis A of the laser beam.

As shown in FIG. 19, a pair of brackets 90a and 90b are fixedly mounted to the base plate 21. A cam shaft 92 is rotatably supported by a pair of bearings 91 and 91 mounted respectively in the brackets 90a and 90b. The cam shaft 92 has one end thereof to which a pulley 93 is fixedly mounted. The pulley 93 is drivingly connected to the motor M (see FIG. 27) through a timing belt and a pulley (both not shown).

The pulley 93 on the cam shaft 92, which is drivingly connected to the motor M, has a diameter five times that of the pulley 63 on the aforementioned cam shaft 62. With such arrangement, the cam shaft 92 makes one revolution while the synchronous shaft 62 makes five revolutions. The cam shaft 92 serves as a driving source for a first moving mechanism 100 for moving the first moving plate 24, a second moving mechanism 110 for moving the second moving plate 27, and a third moving mechanism 120 for moving the aforesaid chuck releasing pin 46.

The first moving mechanism 100 will be described with reference to FIG. 19. A plate cam 101 is fixedly mounted to the cam shaft 92. On the other hand, a bracket 102 is fixedly mounted to the lower surface of the base plate 21. An auxiliary shaft 104 is rotatably supported by a pair of bearings 103 which are mounted respectively in the bracket 102 and the aforesaid bracket 90b.

An elongated link 105 has one end thereof fixedly mounted to the auxiliary shaft 104, and extends therefrom vertically upwardly. A cam follower 106 is supported at a longitudinally intermediate portion of the link 105. A threaded shaft 107b has one end thereof fixed to the other upper end of the link 105. A link 90c is fixedly mounted to the bracket 90b, and extends therefrom vertically upwardly. A threaded shaft 107a has one end thereof fixed to the upper end of the link 90c. A coil spring 107 is interposed under tension between the pair of threaded shafts 107a and 107b to bring the cam follower 106 into contact with the circumferential surface of the plate cam 101.

A link 108 has one end thereof fixedly mounted to the auxiliary shaft 104, and extends therefrom vertically upwardly. The link 108 is formed with a cam face 108a extending vertically. On the other hand, a bracket 109 is fixedly mounted to the lower surface of the first moving plate 24. A cam follower 109a is rotatably supported at the forward end of the bracket 109. The first moving plate 24 is biased upwardly as viewed in FIG. 19 by a spring (not shown). The spring brings the cam follower 109a into contact with the cam face 108a on the link 108.

In the above-described first moving mechanism 100, during one revolution of the cam shaft 92, the cam action between the plate cam 101 and the cam follower 106 causes the auxiliary shaft 104 to be angularly moved about its own axis in a reciprocative manner within a predetermined angular extent. By this reciprocative angular movement, the cam action between the cam face 108a and the cam follower 109a causes the first moving plate 24 to be once reciprocated along the optical axis A of the laser beam. The timing of this reciprocative movement will be described later.

Figure 29:
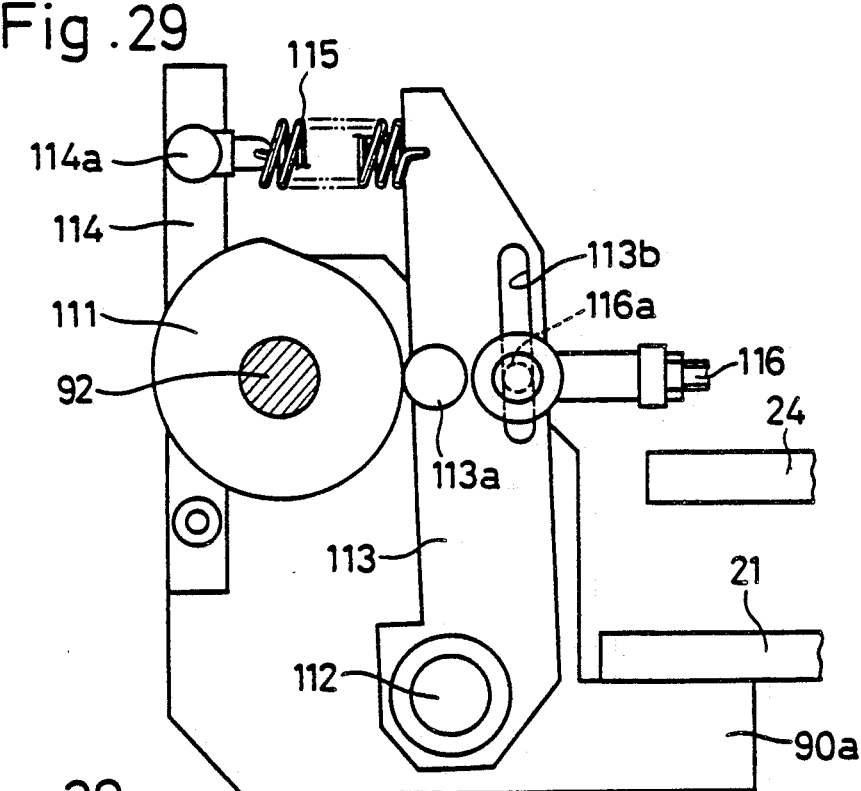
FIG. 29 is a partially cross-sectional enlarged fragmental view of a second moving mechanism illustrated in FIG. 19.

The second moving mechanism 110 will next be described with reference to FIGS. 19 and 29. A plate cam 111 is fixedly mounted to the cam shaft 92. On the other hand, an auxiliary shaft 112 is fixedly mounted, in a cantilevered fashion, to the bracket 90a fixed to the lower surface of the base plate 21. A link 113 has one end thereof mounted on the auxiliary shaft 112 for pivotal movement about an axis thereof, and extends vertically upwardly from the auxiliary shaft 112. A cam follower 113a is rotatably supported at a longitudinally intermediate portion of the link 113. Another link 114 is fixedly mounted to the bracket 90a, and extends therefrom vertically upwardly. A threaded shaft 104a has one end fixed to the upper end of the link 114, and extends therefrom horizontally. A coil spring 115 is interposed under tension between the shaft 114a and the other upper end of the link 113, to bring the cam follower 113a into contact with the peripheral surface of the plate cam 111. The link 113 is formed therein with a slot 113b extending vertically. A slider 116a mounted to one end of a rod 116 is slidably fitted into the slot 113b. The other end of the rod 116 is connected at right angles to one end of another rod 117. The other end of the rod 117 is connected to one end of a bell crank 118 which is pivotally movable about an axis of a pivot 118a. A cam follower 119 is rotatably mounted to the other end of the bell crank 118. On the other hand, the second moving plate 27 is biased to the left-hand direction as viewed in FIG. 19 by a spring (not shown), to bring the side face of the second moving plate 27 into contact with the cam follower 119.

In the above-described second moving mechanism 110, when the cam shaft 92 makes one revolution, the cam action between the plate cam 111 and the cam follower 113a causes the link 113 to be once reciprocated angularly within a predetermined angular extent about the axis of the auxiliary shaft 112. The reciprocative movement is transmitted to the bell crank 118 through the rods 116 and 117, so that the bell crank 118 is angularly moved reciprocatively about the axis of the pivot 118a. The reciprocative angular movement of the bell crank 118 is transmitted to the second moving plate 27 through the cam follower 119, so that the second moving plate 27 is moved reciprocatively in the direction perpendicular to the optical axis A of the laser beam. The timing of this reciprocative movement will be described later.

The third moving mechanism 120 has a cam structure similar to the second moving mechanism 110. The third moving mechanism 120 will be described below with reference to FIG. 19. A plate cam 121 is fixedly mounted to the cam shaft 92. On the other hand, a link 123 has one end thereof pivotally mounted on the aforementioned auxiliary shaft 112, and extends therefrom vertically upwardly. A cam follower 123a is rotatably supported at a longitudinally intermediate portion of the link 123. A spring 125 is interposed under tension between the aforesaid threaded shaft 114a and the other upper end of the link 123, to bring the cam follower 123a into contact with the peripheral surface of the plate cam 121. The link 123 is formed therein with a slot (not shown) extending vertically. A slider (not shown) mounted to one end of a rod 126 is slidably fitted into the slot. The other end of the rod 126 is connected to one end of a bell crank 128 which is pivotally movable about an axis of a pivot 128a. A link 129 has one end thereof which is pivotally mounted to the other end of the bell crank 128. The other end of the link 129 is pivotally connected to the aforesaid chuck releasing pin 46.

In the above-described third moving mechanism 120, when the cam shaft 92 makes one revolution, the cam action between the cam plate 121 and the cam follower 123a causes the link 123 to be once reciprocated angularly within a predetermined angular extent about the axis of the auxiliary shaft 112. This angular reciprocative movement of the link 123 is transmitted to the bell crank 128 through the rod 126, so that the bell crank 128 is reciprocated angularly within a predetermined angular extent about the axis of the pivot 128a. As a result, the chuck releasing pin 46 is once reciprocatively moved along its own axis. The timing of this reciprocative movement will be described later.

In the state prior to the start-up of operation of the apparatus constructed as above, the first spindle 30 is in a position spaced away from the second spindle 35. Moreover, the spindles 30 and 35 are in their respective angular positions where the V-shaped grooves 41a and 51a in the respective support members 41 and 51 are directed vertically upwardly. Further, the chuck releasing pin 46 is in an ejected position, and the forward end 43b of the retainer member 43 is in a position spaced away from the support member 41.

In the state described above, an operator lifts the retainer member 53 up against the biasing force of the leaf spring 54 of the chuck mechanism 50. With the retainer member 53 lifted up, the operator then sets the pipe member 2 into the V-shaped groove 51a in the support member 51. Subsequently, the operator releases his hold from the retainer member 53 to cause the same to retain the pipe member 2 under the biasing force of the leaf spring 54.

Then, the operator turns the operating lever 85 about the axis of the positioning shaft 84, to bring the positioning lever 86 to a position in the vicinity of the forward end of the support member 51 of the chuck mechanism 50. Subsequently, the operator pushes the pusher 56 to bring the end face of the pipe member 2 into abutment against the positioning lever 86. As a result, the pipe member 2 is set at such a position that the one end of the pipe member 2 protrudes a predetermined length from the forward end of the support member 51, and the end face of the one end of the pipe member 2 is coincident with the vertical plane including the optical axis A of the laser beam.

Subsequently, the operator turns the operating lever 85 about the axis of the positioning shaft 84, to return the positioning lever 86 to its initial upstanding position. The operator then lifts the auxiliary leaf spring 45 up, and sets the needle member 1 into the V-shaped groove 41a formed in the support member 41 of the chuck mechanism 40. Subsequently, the operator releases his hold from the auxiliary leaf spring 45 to cause the same to lightly retain the needle member 1 under the biasing force of the leaf spring 45. At this time, the end face 1a of the needle member 1 is located adjacent the end face 2a of the pipe member 2, so that the end of the needle member 1 projects greatly from the forward end of the support member 41 which is in its retracted position.

After the pipe and needle members 2 and 1 have been set in the manner as described above, the motor M is driven. The motor M is stopped after the synchronous shaft 62 makes five revolutions and the cam shaft 92 makes one revolution.

The action during a period for which the synchronous shaft 62 makes first one-fourth revolution, will first be described. By the action of the second moving mechanism 110, the second moving plate 27 is moved in the left-hand direction as viewed in FIG. 19, so that the first spindle 30 and the chuck mechanism 40 are moved in the same left-hand direction. Before the synchronous shaft 62 reaches the rotational angle of the one-fourth revolution, the forward end of the support member 41 of the chuck mechanism 40 reaches a position in the vicinity of the forward end of the support member 51 of the chuck mechanism 50. At this time, the second moving plate 27 is stopped. In the course of this movement, the end face 1a of the needle member 1 is abutted against the end face 2a of the needle member 2, so that the needle member 1 is positioned. On and after this, with movement of the chuck mechanism 40, the needle member 1 slidingly moves relatively to the auxiliary leaf spring 45 and the V-shaped groove 41a. In the latter half of the first one-fourth revolution of the synchronous shaft 62, the third moving mechanism 120 causes the chuck releasing pin 46 to be moved rearwardly. After the second moving plate 27 is stopped, the needle member 1 is retained by the retainer member 43 which is biased by the strong leaf spring 44. Thus, the needle and pipe members 1 and 2 are chucked in such a manner that the end faces 1a and 2a of the respective needle and pipe members 1 and 2 are abutted against each other in the vertical plane including the optical axis A of the laser beam. In this chucked state, the peripheral surfaces of the respective needle and pipe members 1 and 2 are located adjacent the focal position of the laser beam.

During the subsequent one and one-fourth revolutions of the synchronous shaft 62, the laser beam emitting unit 10 (see FIG. 1) outputs pulses of the laser beam. Welding is carried out in such a manner that the pulses of the laser beam are applied to the junction between the needle and pipe members 1 and 2 along the abutting line 3 in a partially overlapped fashion as shown in FIG. 6.

During the subsequent one-fourth revolution of the synchronous shaft 62, the first moving mechanism 100 causes the first moving plate 24 to be moved downwardly as viewed in FIG. 19. Thus, the needle and pipe members 1 and 2 are moved in the direction along the optical axis A of the laser beam, that is, in the direction perpendicular to the aligned axes of the respective needle and pipe members 1 and 2, while the abutting line 3 is maintained coincident with the optical axis A of the laser beam.

Subsequently, the pulses of the laser beam or the continuous laser beam is emitted from the emitting unit 10, while the synchronous shaft 62 makes one revolution. The above-mentioned movement of the first moving plate 24 causes the peripheral surfaces of the respective needle and pipe members 1 and 2 to be moved away from the focal position of the laser beam as shown in FIG. 8, so that the spot diameter of the laser beam on the peripheral surfaces of the respective needle and pipe members 1 and 2 increases. Accordingly, annealing is carried out along the welded portion over the width wider than the welded portion and at the temperature lower than the melting temperature.

In the course of the subsequent two revolutions of the synchronous shaft 62, the second moving plate 27 is moved in the right-hand direction as viewed in FIG. 19 by the second moving mechanism 110, and is returned to the initial position. Since the biasing force of the leaf spring 44 of the chuck mechanism 40 is considerably stronger than that of the leaf spring 54 of the chuck mechanism 50, the pipe member 2 welded to the needle member 1 is moved together with the same in the right-hand direction as viewed in FIG. 19, and is drawn out of the chuck mechanism 50. Since, during this movement of the pipe member 2, the laser beam is maintained outputted, the peripheral surface of the pipe member 2 is annealed in a helical fashion. As a consequence, the entire peripheral surface of the pipe member 2 is annealed.

In the course of the subsequent last one-fourth revolution of the synchronous shaft 62, the third moving mechanism 120 causes the chuck releasing pin 46 to be moved forwardly, that is, in the left-hand direction as viewed in FIG. 19, so that the needle member 1 is released from the chucked state due to the biasing force of the strong leaf spring 44, and is retained only by the auxiliary spring 45. Moreover, in the course of the last one-fourth revolution of the synchronous shaft 62, the first moving mechanism 100 causes the first moving plate 24 to be moved upwardly as viewed in FIG. 19, and to be returned to the initial position.

Figure 30:
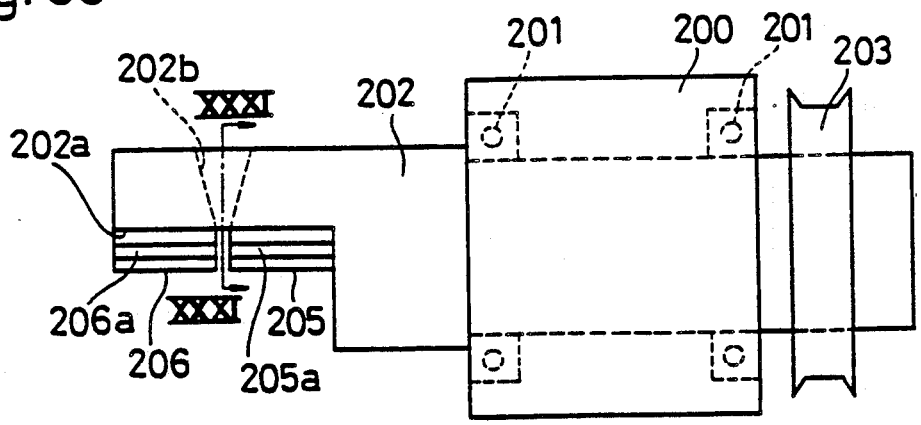
FIG. 30 is a plan view of another aspect of means for supporting and rotating a needle member and a pipe member.
Figure 31:
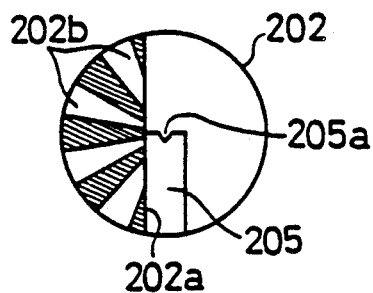
FIG. 31 is a cross-sectional view taken along line XXXI—XXXI in FIG. 30.

FIGS. 30 and 31 show another embodiment of the invention, which comprises different arrangement for rotating the needle and pipe members about their respective axes. In the arrangement illustrated in FIGS. 30 and 31, a bracket 200 is fixedly mounted to a moving plate (not shown). A spindle 202 is rotatably supported by a pair of bearings 201 and 201 mounted in the bracket 200. A pulley 203 is fixedly mounted to the proximal end of the spindle 202, and is connected to the pulley fixedly mounted to an output shaft of a motor (not shown) through the timing belt. A pair of chuck mechanisms for chucking respectively the needle and pipe members are mounted to the forward end of the spindle 202. Each of these chuck mechanisms is similar in construction to the chuck mechanism 50 for the pipe member in the above-mentioned embodiment illustrated in FIGS. 21 through 23, and the detailed description and illustration of the chuck mechanisms will therefore be omitted. In FIGS. 30 and 31, only support members 205 and 206 of the respective chuck mechanisms are shown. A forward end of the spindle 202 is cut out to form a planar face 202a extending parallel to the axis of the spindle 202. The support members 205 and 206 are fixedly mounted to the planar face 202a, and are spaced a slight distance from each other. V-shaped grooves 205a and 206a formed respectively in the support members 205 and 206 are located in alignment with each other, so that the axes of the respective needle and pipe members set respectively in the V-shaped grooves 205a and 206a are aligned with the axis of the spindle 202. The forward end portion of the spindle 202 is formed therein with a plurality of bores 202b at a position corresponding to the gap between the support members 205 and 206. As best shown in FIG. 31, the bores 202b extend radially outwardly from the axis of the spindle 202.

In the arrangement illustrated in FIGS. 30 and 31, the forward end of the positioning lever (86: see FIG. 19) is moved to a position between the support members 205 and 206, and the end face of the needle member is abutted against the positioning lever and is positioned thereby. In this manner, the needle member is set in the V-shaped groove 205a formed in the support member 205, and is retained by the retainer member biased by the leaf spring (not shown). Then, the positioning lever is moved away from the gap between the support members 205 and 206 and, subsequently, the end face of the pipe member is abutted against the end face of the needle member to position the pipe member. In this manner, the pipe member is set in the V-shaped groove 206a formed in the support member 206, and is retained by the retainer member biased by the leaf spring (not shown). Then, while rotating the spindle 202 about its own axis, the pulses of the laser beam from the laser beam emitting unit (not shown) are applied to the junction between the needle and pipe members along the abutting line, to thereby carry out welding.

During application of the pulses of the laser beam, the forward end portion of the spindle 202 intercepts the optical axis of the laser beam within a predetermined angular extent. Since, however, the bores 202b are formed in the forward end portion of the spindle 202, the pulses of the laser beam can be applied to the junction between the needle and pipe members, with the result that welding can be carried out substantially along the entire circumferential length of the abutting line. The laser beam emitting unit is controlled in such a synchronous manner that the pulses of the laser beam are successively emitted each time the bores 202b are successively aligned with the optical axis of the laser beam. If it is desired to partially weld the junction between the needle and pipe members only at, for example, two locations, not along the entire circumferential length of the abutting line, the bores 202b are unnecessary and are dispensed with. After the welding, the moving plate supporting the spindle 202 is moved in the direction along the optical axis of the laser beam in a manner similar to that of the previously mentioned embodiment. Subsequently, the laser beam is applied to the welded portion while rotating the spindle 202 about its own axis, thereby carrying out annealing.

The arrangement of the embodiment illustrated in FIGS. 30 and 31 is such that the needle and pipe members are supported by the single spindle 202 and are rotated thereby. Accordingly, as compared with the arrangement in which, as is in the previous embodiment, the needle and the pipe members are supported respectively by the spindles 30 and 35 independent of each other and are rotated respectively thereby, it is possible for the arrangement illustrated in FIGS. 30 and 31 to dispense with the mechanism for synchronism such as, for example, the synchronous shaft 62 and the associated components. It is needless to say that the arrangement illustrated in FIGS. 30 and 31 can be applied to the method in which welding is carried out only at a plurality of locations on the abutting line, like the previous embodiment shown in FIGS. 19 through 29.

Figure 32:
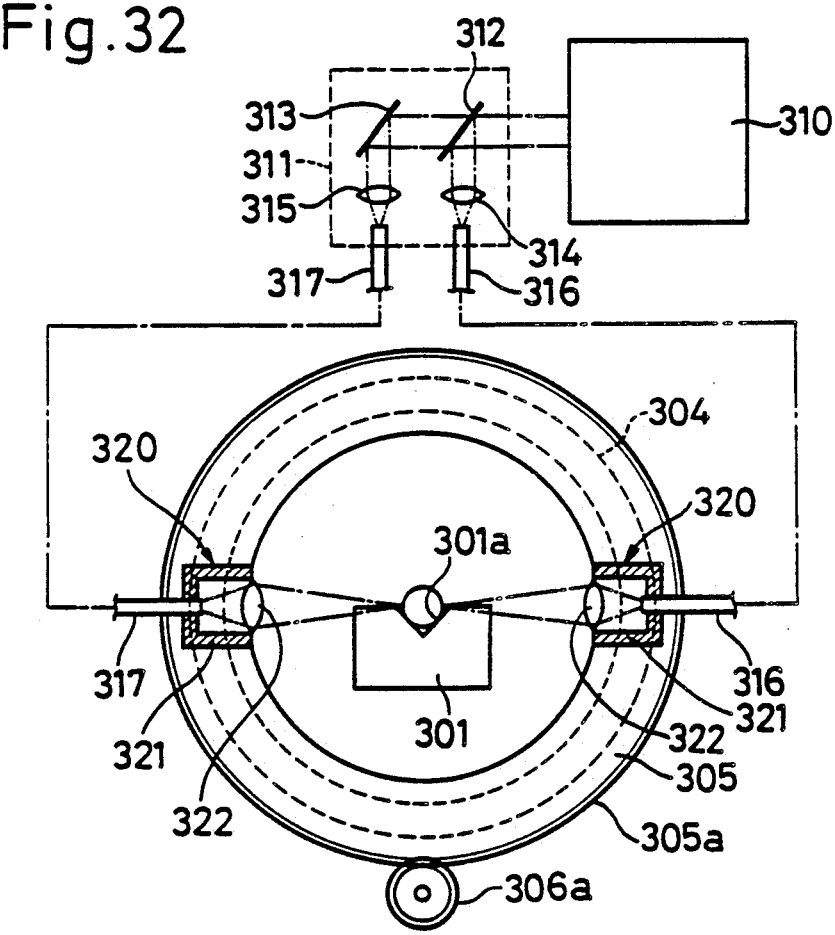
FIG. 32 is a front elevational view showing a surgical needle manufacturing apparatus according to another embodiment of the invention.
Figure 33:
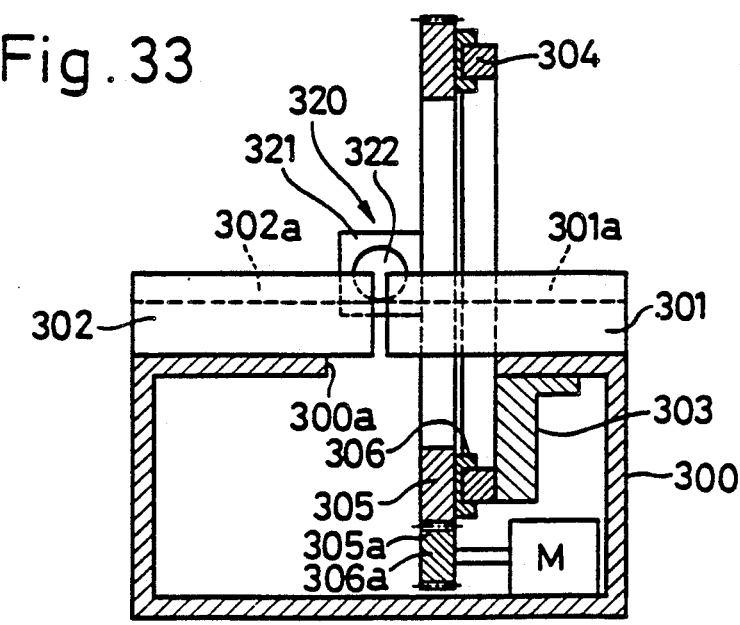
FIG. 33 is a vertical cross-sectional view of the apparatus illustrated in FIG. 32.

FIGS. 32 and 33 show still another embodiment of the invention, in which while the needle and pipe members are maintained stationary, the laser beam emitting unit moves around the aligned axes of the respective needle and pipe members. Specifically, a casing 300 has a top wall formed therein with an opening 300a. A pair of support members 301 and 302 are fixedly mounted to an upper surface of the top wall of the casing 300. The support members 301 and 302 have their respective upper surfaces which are formed respectively with V-shaped grooves 301a and 302a aligned with each other. The needle and pipe members can be set respectively in the V-shaped grooves 301a and 302a. Positioning and chucking of these needle and pipe members are similar to those in the previous embodiment described with reference to FIGS. 19 through 29, and the description of the positioning and chucking will therefore be omitted. A ring-like rail 304 is fixedly mounted to the casing 300 through a bracket 303. A plurality of circumferentially spaced sliders 306 are fixed to the ring-like support member 305, and are supported by the rail 304 through respective bearings or the like (not shown). The support member 305 has a peripheral surface formed with teeth 305a. A gear 306a fixedly mounted to the output shaft of the motor M is in mesh with the teeth 305a of the support member 305. Accordingly, rotation of the motor M causes the support member 305 to be rotated. A center of rotation of the support member 305, in other words, a center of the radius of curvature of the support member 305 is coincident with the aligned axes of the respective needle and pipe members set respectively in the V-shaped grooves 301a and 302a formed in the respective support members 301 and 302.

On the other hand, a collimated laser beam is outputted from a laser beam generating source 310 mounted stationarily, toward a laser beam dividing unit 311 mounted stationarily. The laser beam dividing unit 311 comprises a semi-transparent mirror 312 and a mirror 313, and a pair of condenser optical systems 314 and 315 including their respective convex lenses optically connected respectively to the mirrors 312 and 313. Only half the collimated laser beam generated at the laser beam generating source 310 is reflected by the semi-transparent mirror 312, and is directed toward the condenser optical system 314. The laser beam is condensed by the condenser optical system 314, and is supplied to one end of an optical fiber 316. The remaining half of the collimated laser beam transmitted through the semi-transparent mirror 312 is reflected by the mirror 313 and is directed to the second condenser optical system 315. The laser beam from the mirror 313 is condensed by the condenser optical system 315, and is supplied to one end of a second optical fiber 317. The other ends of the respective optical fibers 316 and 317 are connected respectively to a pair of laser beam emitting sections 320 and 320. The pair of laser beam emitting sections 320 and 320 are circumferentially spaced 180 degrees from each other so that they face each other. Each laser beam emitting section 320 comprises a casing 321 fixedly mounted to the support member 305, and a condenser optical system 322 including a convex lens fixed to the casing 321. The other ends of the respective optical fibers 316 and 317 extend through the rear walls of the respective casings 321, and face the respective condenser optical systems 322 and 322, to supply the laser beams thereto. Each condenser optical system 322 condenses the corresponding laser beam to supply the same onto the abutting line between the needle and pipe members. Each laser beam has an optical axis intersected with the aligned axes of the respective needle and pipe members.

The arrangement of the embodiment illustrated in FIGS. 32 and 33 is such that while angularly moving the support member 305 by the motor M about the aligned axes of the respective needle and pipe members, the respective laser beams from the pair of facing laser beam emitting sections 320 and 320 are simultaneously supplied onto the abutting line. With such arrangement, if it is desired to weld the needle and pipe members to each other along the entire circumferential length of the abutting line, it is sufficient to angularly move the support member 305 substantially through 180 degrees or through an angular extent slightly larger than 180 degrees.

Three or more laser beam emitting sections may be mounted to the support member 305. In this case, if it is desired to carry out welding along the entire circumferential length of the abutting line, it is possible to further narrow the angular extent through which the support member 305 is angularly moved. Moreover, only a single laser beam emitting section may be mounted to the support member 305.

When it is desired to carry out welding only at a plurality of locations spaced from each other along the abutting line, it is not required for the support member to be angularly moved about the aligned axes of the respective needle and pipe members, but the support member may be fixed to the casing, if a plurality of laser beam emitting sections corresponding in number to the locations to be welded are mounted to the support member.

What is claimed is:

1. A method of manufacturing a surgical needle, comprising the steps of: abutting an end face of a pipe member against a proximal end face of a needle member to form an abutting line which is annular in appearance; and supplying a beam energy from beam energy emitting means, toward said abutting line, from a direction substantially perpendicular to said needle and pipe members thereby welding said needle and pipe members to each other to form a welded portion therebetween,
wherein the beam energy is supplied in such a manner that at least a part of the step of supplying the beam energy toward the abutting line is carried out in an inert gas atmosphere.

2. A method of manufacturing a surgical needle according to claim 1, wherein said beam energy is supplied to said abutting line along an entire circumferential length thereof, to carry out said welding.

3. A method of manufacturing a surgical needle according to claim 2, wherein said beam energy is supplied to said abutting line so as to be overlapped along a part of said abutting line, to carry out said welding.

4. A method of manufacturing a surgical needle according to claim 2, further comprising the step of, prior to said welding, supplying the beam energy to a plurality locations on said abutting line, to carry out weak tack-welding.

5. A method of manufacturing a surgical needle according to claim 2, further comprising the steps of varying, axially of said beam energy, a distance between said beam energy emitting means and said needle and pipe members, to increase a spot diameter of said beam energy on the peripheral surfaces of the respective needle and pipe members, and supplying said beam energy to said welded portion along the same, to anneal an annular region wider than said welded portion.

6. A method of manufacturing a surgical needle according to claim 1, further comprising the step of supplying said beam energy is supplied only to a plurality of peripherally spaced locations on said abutting line.

7. A method of manufacturing a surgical needle according to claim 1, further comprising the step of, while rotating said needle and pipe members about their respective axes with said needle and pipe members abutted against each other, applying the beam energy from the stationary beam energy emitting means, to the abutting line, to carry out said welding.

8. A method of manufacturing a surgical needle according to claim 7, further comprising the steps of varying, axially of said beam energy, a distance between said beam energy emitting means and said needle and pipe members, to increase a spot diameter of said beam energy on the peripheral surfaces of the respective needle and pipe members, and applying the beam energy to the peripheral surface of said pipe member while said needle and pipe members are moved along their respective axes and are rotated about their respective axes, thereby annealing said pipe member.

9. A method of manufacturing a surgical needle according to claim 1, further comprising the step of, with said needle and pipe members abutted against each other and maintained stationary, supplying said beam energy to said abutting line, while moving said beam energy emitting means around the axes of the respective needle and pipe members, and while intersecting an optical axis of said beam energy with the axes of the respective needle and pipe members.

10. A method of manufacturing a surgical needle according to claim 1, further comprising the step of, prior to the welding due to said beam energy, annealing said pipe member.

11. A method of manufacturing a surgical needle according to claim 1, in which the inert gas of the inert gas atmosphere is blown from a nozzle toward the abutting line.

12. A method of manufacturing a surgical needle comprising the steps of: wrapping up a plurality of pipe members in a heat resistant foil; supplying heat from the outside to the pipe members wrapped up in said foil to anneal said pipe members; removing said annealed pipe members from the foil; abutting an end face of each pipe member against a proximal end face of a needle member to form an abutting line which is annular in appearance; and supplying a beam energy from beam energy emitting means, toward said abutting line, from a direction substantially perpendicular to said needle and pipe members thereby welding said needle and pipe members to each other to form a welded portion therebetween.

13. An apparatus for manufacturing a surgical needle, comprising:
  (a) beam energy emitting means;
  (b) rotational support means for supporting a needle member and a pipe member in such a manner that axes of the needle and pipe members extend perpendicularly to an axis of a laser beam emitted from said beam energy emitting means and in such a manner that an end face of said needle member and an end face of said pipe member are abutted against each other at a location coincident with said axis of the laser beam, said rotational support means also rotating said needle and pipe members about their respective axes; and
  (c) drive means for rotating said rotational support means;
  wherein said rotational support means comprises a single rotary structure connected to said drive means which has formed therein with at least one bore extending radially outwardly from the axis of said rotary structure, to permit the beam energy to pass through said bore and which further comprises two support means spaced apart from each other and supporting said needle and pipe members in such a manner that the axes of the needle and pipe members are aligned with an axis of said rotary structure.

14. An apparatus for manufacturing a surgical needle according to claim 13, further comprising moving means for moving said pair of rotary structures toward and away from each other in a direction perpendicular to said axis of the beam energy.

15. An apparatus for manufacturing a surgical needle according to claim 13, further comprising moving means for moving said rotational support means in a direction perpendicular to the axes of the respective needle and pipe members, to increase a spot diameter of the beam energy applied to the peripheral surfaces of the respective needle and pipe members.

16. An apparatus for manufacturing a surgical needle, comprising a laser beam generating source arranged stationarily, a laser beam emitting section receiving a laser beam from said laser beam generating source through an optical fiber, said laser beam emitting section condensing the laser beam to emit the condensed laser beam, guide means at least including an arcuate portion, moving means for moving said laser beam emitting section along said guide means while maintaining such a posture that an optical axis of the laser beam emitted from said laser beam emitting section passes through a central axis of a radius of curvature of said arcuate portion of said guide means, and support means supporting said needle and pipe members while maintaining them stationary in such a manner that said needle and pipe members are abutted against each other, at a location substantially coincident with a plane including the optical axis of said laser beam and that the axes of the respective needle and pipe members are coincident with the central axis of the radius of curvature of said guide means.

* * * * *